(12) United States Patent
Yoo et al.

(10) Patent No.: US 10,691,407 B2
(45) Date of Patent: Jun. 23, 2020

(54) METHODS AND SYSTEMS FOR ANALYZING SPEECH DURING A CALL AND AUTOMATICALLY MODIFYING, DURING THE CALL, A CALL CENTER REFERRAL INTERFACE

(71) Applicant: Kyruus, Inc., Boston, MA (US)

(72) Inventors: Julie Keunhee Yoo, Boston, MA (US); Graham Stewart Gardner, Sudbury, MA (US); Vinay Seth Mohta, Newton, MA (US); Jakov Kucan, Cambridge, MA (US)

(73) Assignee: Kyruus, Inc., Boston, MA (US)

( * ) Notice: Subject to any disclaimer, the term of this patent is extended or adjusted under 35 U.S.C. 154(b) by 106 days.

(21) Appl. No.: 15/840,586

(22) Filed: Dec. 13, 2017

(65) Prior Publication Data

US 2018/0165062 A1 Jun. 14, 2018

Related U.S. Application Data

(60) Provisional application No. 62/433,882, filed on Dec. 14, 2016.

(51) Int. Cl.
*A61B 5/00* (2006.01)
*G06F 3/16* (2006.01)
(Continued)

(52) U.S. Cl.
CPC .............. *G06F 3/167* (2013.01); *G10L 15/02* (2013.01); *G10L 15/22* (2013.01); *G10L 15/26* (2013.01);
(Continued)

(58) Field of Classification Search
CPC .............................. A61B 5/0002; G10L 17/26
See application file for complete search history.

(56) References Cited

U.S. PATENT DOCUMENTS 4,459,361 A 7/1984 Gefter
5,225,163 A 7/1993 Andrews
(Continued)

FOREIGN PATENT DOCUMENTS

JP 2005250841 B2 9/2005
KR 20090105715 B1 10/2009
(Continued)

OTHER PUBLICATIONS

Final Office Action issued in U.S. Appl. No. 14/537,115 dated Oct. 17, 2017, 25 pages.
(Continued)

*Primary Examiner* — Feng-Tzer Tzeng
(74) *Attorney, Agent, or Firm* — Blueshift IP, LLC; Cynthia M. Gilbert

(57) ABSTRACT

A method for analyzing speech generated during a call to generate a potential referral and automatically modifying, during the call, a user interface displaying data associated with the analyzed speech, includes analyzing, by an analysis engine, during a call by a patient to a call center operator, data generated during the call, the data received from a second computing device. The method includes identifying patient data associated with the patient. The method includes determining at least one requirement of the patient based upon the identified patient data and the analysis. The method includes generating a potential referral to a physician for the patient, the physician having a profile that satisfies the determined at least one requirement. The method includes modifying a user interface displayed to the call center, during the call, the modification to the display including addition of an identification of the potential referral.

13 Claims, 13 Drawing Sheets

(51) Int. Cl.

| | | |
|---|---|---|
| *G16H 80/00* | (2018.01) | |
| *G10L 15/22* | (2006.01) | |
| *G10L 25/63* | (2013.01) | |
| *G10L 15/02* | (2006.01) | |
| *G10L 15/26* | (2006.01) | |
| *G16H 40/20* | (2018.01) | |
| *G10L 25/66* | (2013.01) | |
| *G10L 15/18* | (2013.01) | |
| *H04M 3/51* | (2006.01) | |
| *G10L 15/08* | (2006.01) | |

(52) U.S. Cl.
CPC ............. *G10L 25/63* (2013.01); *G10L 25/66* (2013.01); *G16H 40/20* (2018.01); *G16H 80/00* (2018.01); *A61B 5/0002* (2013.01); *G10L 15/1815* (2013.01); *G10L 2015/088* (2013.01); *H04M 3/5183* (2013.01)

(56) References Cited

U.S. PATENT DOCUMENTS

| | | |
|---|---|---|
| 5,875,431 A | 2/1999 | Heckman |
| 5,918,208 A | 6/1999 | Javitt |
| 6,223,164 B1 | 4/2001 | Seare |
| 7,062,483 B2 | 6/2006 | Ferrari |
| 7,065,528 B2 | 6/2006 | Herz |
| 7,158,979 B2 | 1/2007 | Iverson |
| 7,222,079 B1 | 5/2007 | Seare |
| 7,325,201 B2 | 1/2008 | Ferrari |
| 7,428,528 B1 | 9/2008 | Ferrari |
| 7,444,291 B1 | 10/2008 | Prasad |
| 7,567,957 B2 | 7/2009 | Ferrari |
| 7,617,184 B2 | 11/2009 | Ferrari |
| 7,620,560 B2 | 11/2009 | Dang |
| 7,640,175 B1 | 12/2009 | Prasad |
| 7,698,155 B1 | 4/2010 | Prasad |
| 7,711,577 B2 | 5/2010 | Dust |
| 7,711,660 B1 | 5/2010 | Gentile |
| 7,725,333 B2 | 5/2010 | Dang |
| 7,739,128 B2 | 6/2010 | Farris |
| 7,774,216 B2 | 8/2010 | Dang |
| 7,774,252 B2 | 8/2010 | Seare |
| 7,792,687 B2 | 9/2010 | Farris |
| 7,801,749 B2 | 9/2010 | Lynn |
| 7,856,362 B2 | 12/2010 | Walker |
| 7,865,457 B1 | 1/2011 | Ravin |
| 7,917,374 B2 | 3/2011 | Walker |
| 7,917,525 B2 | 3/2011 | Rawlings |
| 7,966,196 B2 | 6/2011 | Walker |
| 7,979,290 B2 | 7/2011 | Dang |
| 8,010,460 B2 | 8/2011 | Work et al. |
| 8,036,916 B2 | 10/2011 | Dust et al. |
| 8,082,172 B2 | 12/2011 | Chao |
| 8,249,887 B2 | 8/2012 | Firminger |
| 8,249,888 B2 | 8/2012 | Firminger |
| 8,260,626 B2 | 9/2012 | Firminger |
| 8,260,729 B2 | 9/2012 | Firminger |
| 8,260,807 B2 | 9/2012 | Firminger |
| 8,265,945 B2 | 9/2012 | Firminger |
| 8,271,295 B1 | 9/2012 | Miller |
| 8,271,524 B2 | 9/2012 | Firminger |
| 8,285,585 B2 | 10/2012 | Chao |
| 8,311,846 B2 | 11/2012 | Firminger |
| 8,311,850 B2 | 11/2012 | Johnson |
| 8,321,233 B2 | 11/2012 | Firminger |
| 8,392,205 B2 | 3/2013 | Firminger |
| 8,538,779 B1 | 9/2013 | Whibbs |
| 8,756,075 B1 | 6/2014 | Sultan |
| 9,058,635 B1 | 6/2015 | Rybkin |
| 2001/0041990 A1 | 11/2001 | Javitt |
| 2002/0042786 A1 | 4/2002 | Scarborough |
| 2002/0051020 A1 | 5/2002 | Ferrari |
| 2002/0065758 A1 | 5/2002 | Henley |
| 2002/0083039 A1 | 6/2002 | Ferrari |
| 2002/0120469 A1 | 8/2002 | Javitt |
| 2002/0133386 A1 | 9/2002 | Chishti |
| 2002/0152096 A1 | 10/2002 | Falchuk |
| 2003/0097357 A1 | 5/2003 | Ferrari |
| 2003/0130873 A1 | 7/2003 | Nevin |
| 2003/0140037 A1 | 7/2003 | Deh-Lee |
| 2004/0116785 A1* | 6/2004 | Bulat ............... A61B 5/0002 600/300 |
| 2005/0075902 A1 | 4/2005 | Wager |
| 2006/0149589 A1 | 7/2006 | Wager |
| 2007/0055610 A1 | 3/2007 | Palestrant |
| 2007/0055611 A1 | 3/2007 | Palestrant |
| 2007/0055612 A1 | 3/2007 | Palestrant |
| 2007/0061217 A1 | 3/2007 | Palestrant |
| 2007/0061218 A1 | 3/2007 | Palestrant |
| 2007/0061219 A1 | 3/2007 | Palestrant |
| 2007/0083403 A1 | 4/2007 | Baldwin |
| 2007/0083505 A1 | 4/2007 | Ferrari |
| 2007/0106658 A1 | 5/2007 | Ferrari |
| 2007/0143128 A1 | 6/2007 | Tokarev |
| 2007/0174252 A1 | 7/2007 | Rawlings |
| 2007/0299690 A1 | 12/2007 | Frank |
| 2008/0021266 A1 | 1/2008 | Laham |
| 2008/0027783 A1 | 1/2008 | Hughes |
| 2008/0164998 A1 | 7/2008 | Scherpbier et al. |
| 2008/0243581 A1 | 10/2008 | Jennings |
| 2008/0270180 A1 | 10/2008 | Sholtis |
| 2008/0306952 A1 | 12/2008 | Lynn |
| 2009/0055404 A1 | 2/2009 | Heiden |
| 2009/0089092 A1 | 4/2009 | Johnson |
| 2009/0125348 A1 | 5/2009 | Rastogi |
| 2009/0157425 A1 | 6/2009 | Walker |
| 2009/0164252 A1 | 6/2009 | Morris |
| 2009/0259488 A1 | 10/2009 | Gounares |
| 2009/0319523 A1 | 12/2009 | Anderson |
| 2010/0042431 A1 | 2/2010 | O'Connor |
| 2010/0070300 A1 | 3/2010 | Anderson |
| 2010/0082361 A1 | 4/2010 | Dennen |
| 2010/0100395 A1 | 4/2010 | Prasad |
| 2010/0114900 A1 | 5/2010 | Anderson |
| 2010/0145722 A1 | 6/2010 | Zalta |
| 2010/0174688 A1 | 7/2010 | Anumakonda |
| 2010/0185496 A1 | 7/2010 | Hahn |
| 2010/0287190 A1 | 11/2010 | Anderson |
| 2010/0312713 A1 | 12/2010 | Keltner |
| 2010/0325148 A1 | 12/2010 | Anderson |
| 2011/0055167 A1 | 3/2011 | Howey |
| 2011/0066475 A1 | 3/2011 | Sullivan |
| 2011/0066954 A1 | 3/2011 | Zuber |
| 2011/0110422 A1 | 5/2011 | Nagori |
| 2011/0112853 A1 | 5/2011 | Tong |
| 2011/0119207 A1 | 5/2011 | Tong |
| 2011/0184926 A1 | 7/2011 | Lee |
| 2011/0191122 A1 | 8/2011 | Kharraz Tavakol |
| 2012/0095931 A1 | 4/2012 | Gurion |
| 2012/0197906 A1 | 8/2012 | Landau |
| 2012/0254312 A1 | 10/2012 | Patel |
| 2012/0290311 A1 | 11/2012 | Tara |
| 2013/0031090 A1 | 1/2013 | Posse |
| 2013/0042007 A1 | 2/2013 | Linton |
| 2013/0096991 A1 | 4/2013 | Gardner |
| 2013/0111363 A1 | 5/2013 | Linton |
| 2013/0173264 A1* | 7/2013 | Kiss ............... G10L 17/26 704/231 |
| 2013/0332207 A1 | 12/2013 | Brunel |
| 2014/0052569 A1 | 2/2014 | Yoo |
| 2014/0143352 A1 | 5/2014 | Yegnashankaran |
| 2014/0164952 A1 | 6/2014 | Allen |
| 2014/0222702 A1 | 8/2014 | Jennings |
| 2014/0303760 A1 | 10/2014 | Yost, III |
| 2014/0344035 A1 | 11/2014 | Hewett |
| 2015/0006259 A1 | 1/2015 | Yoo |
| 2015/0058056 A1 | 2/2015 | Comerford |
| 2015/0088539 A1 | 3/2015 | Yoo |
| 2015/0134388 A1 | 5/2015 | Yoo |

(56) References Cited

U.S. PATENT DOCUMENTS

2016/0042477 A1 2/2016 Gardner
2016/0307140 A1 10/2016 Yoo

FOREIGN PATENT DOCUMENTS

| WO | 0180116 A1 | 10/2001 |
| WO | 02080056 A2 | 10/2002 |
| WO | 05038580 A2 | 4/2005 |
| WO | 07145900 A2 | 12/2007 |

OTHER PUBLICATIONS

Final Rejection issued in U.S. Appl. No. 13/653,675, Gardner et al., dated Jan. 9, 2015, 18 pages.
Final Rejection issued in U.S. Appl. No. 14/922,305, Gardner et al., dated May 24, 2018, 19 pages.
International Search Report and Written Opinion for PCT/US2012/060562, dated Mar. 29, 2013, 10 pages.
International Search Report and Written Opinion for PCT/US2014/064902, dated Feb. 24, 2015, 9 pages.
Non-Final Office Action issued in U.S. Appl. No. 14/537,115 dated Jun. 18, 2018, 33 pages.
Non-Final Office Action issued in U.S. Appl. No. 14/537,115 dated Mar. 2, 2017, 16 pages.
Non-Final Rejection issued in related U.S. Appl. No. 14/059,499, Yoo et al., dated Apr. 28, 2015, 22 pages.
Non-Final Rejection issued in related U.S. Appl. No. 14/492,566, Yoo et al., dated Jun. 15, 2018, 21 pages.
Non-Final Rejection issued in U.S. Appl. No. 13/653,675, Gardner et al., dated Aug. 27, 2014, 18 pages.
Non-Final Rejection issued in U.S. Appl. No. 13/653,675, Gardner et al., dated May 4, 2015, 22 pages.
U.S. Appl. No. 13/653,675, filed Oct. 17, 2013.
U.S. Appl. No. 14/059,499, filed Oct. 22, 2013.
U.S. Appl. No. 14/305,042, filed Jun. 16, 2014.
U.S. Appl. No. 15/195,367, filed Jun. 28, 2016.
U.S. Appl. No. 14/537,115, filed Nov. 10, 2014.
Final Office Action issued in U.S. Appl. No. 14/922,305 dated Feb. 12, 2019, 32 pages.
Final Rejection issued in related U.S. Appl. No. 14/492,566, Yoo et al., dated Dec. 27, 2018, 15 pages.
Non-Final Office Action issued in U.S. Appl. No. 14/922,305 dated Oct. 5, 2018, 22 pages.
Non-Final Rejection issued in related U.S. Appl. No. 15/195,367, Yoo et al., dated Oct. 13, 2017, 9 pages.
U.S. Appl. No. 13/653,675, filed Oct. 17, 2012.
U.S. Appl. No. 14/059,499, filed Oct. 17, 2012.
U.S. Appl. No. 14/922,305, filed Oct. 26, 2015.
U.S. Appl. No. 14/305,042, filed Jun. 28, 2016.
U.S. Appl. No. 14/337,115, filed Nov. 10, 2014.
U.S. Appl. No. 14/492,566, filed Sep. 22, 2014.
Non-Final Rejection issued in U.S. Appl. No. 14/492,566, Yoo et al., dated Nov. 14, 2019, 24 pages.

\* cited by examiner

Fig. 2B

Table 330

| Type | Total No. | Physician Name | Physician Percentage | Equal to or Higher than Threshold? | How Much Reallocation Required? |
|---|---|---|---|---|---|
| Heart Surgery | 200/year | Smith | 41 | Yes | n/a |
|  |  | Jones | 40 | Yes | n/a |
|  |  | Williams | 14 | No | 6% |
|  |  | Miller | 5 | No | 5% |
| Brain Surgery | 150/year | Smith | 5 | No | 5% |
|  |  | Jones | 5 | No | 5% |
|  |  | Williams | 30 | Yes | n/a |
|  |  | Miller | 60 | Yes | n/a |

METHODS AND SYSTEMS FOR ANALYZING SPEECH DURING A CALL AND AUTOMATICALLY MODIFYING, DURING THE CALL, A CALL CENTER REFERRAL INTERFACE

CROSS-REFERENCE TO RELATED APPLICATIONS

This application claims priority from U.S. Provisional Patent Application Ser. No. 62/433,882, filed on Dec. 14, 2016, entitled "Methods and Systems for Analyzing Speech to Generate a Potential Referral," which is hereby incorporated by reference.

BACKGROUND

The disclosure relates to real-time analysis of data generated from speech during a call to a call center and automatically modifying call center interfaces. More particularly, the methods and systems described herein relate to analyzing speech generated during a call to generate a potential referral and automatically modifying, during the call, a user interface displaying data associated with the analyzed speech.

Conventionally, professionals' profiles are used for many purposes including, for example, identifying industry opportunities for professionals, or identifying key opinion leaders. However, existing approaches to generating profiles and identifying opportunities or professionals are typically manual or driven by secondary variables. Manual approaches therefore may be time-consuming (for example, cold-calling providers and asking for suggestions). Additionally, typical technologies tend to be unable to keep up with the velocity, volume, and variety of data required to populate professional profiles. As a result, conventional methods for matching a patient need, as presented to a call center operator, to a physician typically depend on intuition and the limitations of the operator, and the record-keeping system available to the operator, as opposed to bias-free, data-driven identification of appropriate physicians for a potential referral while also conforming to the constraints associated with a patient.

BRIEF SUMMARY

In one aspect, a method for analyzing speech generated during a call to generate a potential referral and automatically modifying, during the call, a user interface displaying data associated with the analyzed speech includes analyzing, by an analysis engine executing on a first computing device, during a call by a patient to a call center operator, data generated during the call, the data received from a second computing device. The method includes identifying, by the analysis engine, patient data associated with the patient, responsive to the analysis. The method includes determining, by the analysis engine, at least one requirement of the patient based upon the identified patient data and the analysis. The method includes generating, by the analysis engine, a potential referral to a physician for the patient, the physician having a profile that satisfies the determined at least one requirement. The method includes modifying, by the analysis engine, a user interface displayed to the call center, during the call, the modification to the display including addition of an identification of the potential referral.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIG. 2B is a screen shot depicting one embodiment of profiles generated by a profile generator;

FIG. 3D is a block diagram depicting one embodiment of a data structure generated by an analysis engine and storing determined calculations.

DETAILED DESCRIPTION

In some embodiments, the methods and systems described herein relate to analyzing speech to generate a potential referral. In one of these embodiments, the methods and systems described herein provide functionality for extracting patient information during telephone conversations, and use the extracted information to generate potential referrals to physicians, using stored physician profiles. Some embodiments use patients' currently or previously expressed preferences to select optimal matches with physicians. Some embodiments take feedback from a patient or call center operator in real time to refine matches. Additional embodiments dynamically schedule appointments with the referred, profiled physicians on behalf of a patient, with or without direction from an operator. Before describing such methods and systems in detail, however, a description is provided of a network which may be modified in order to execute the methods and systems described below, resulting in new, non-generic systems.

Figure 1A:
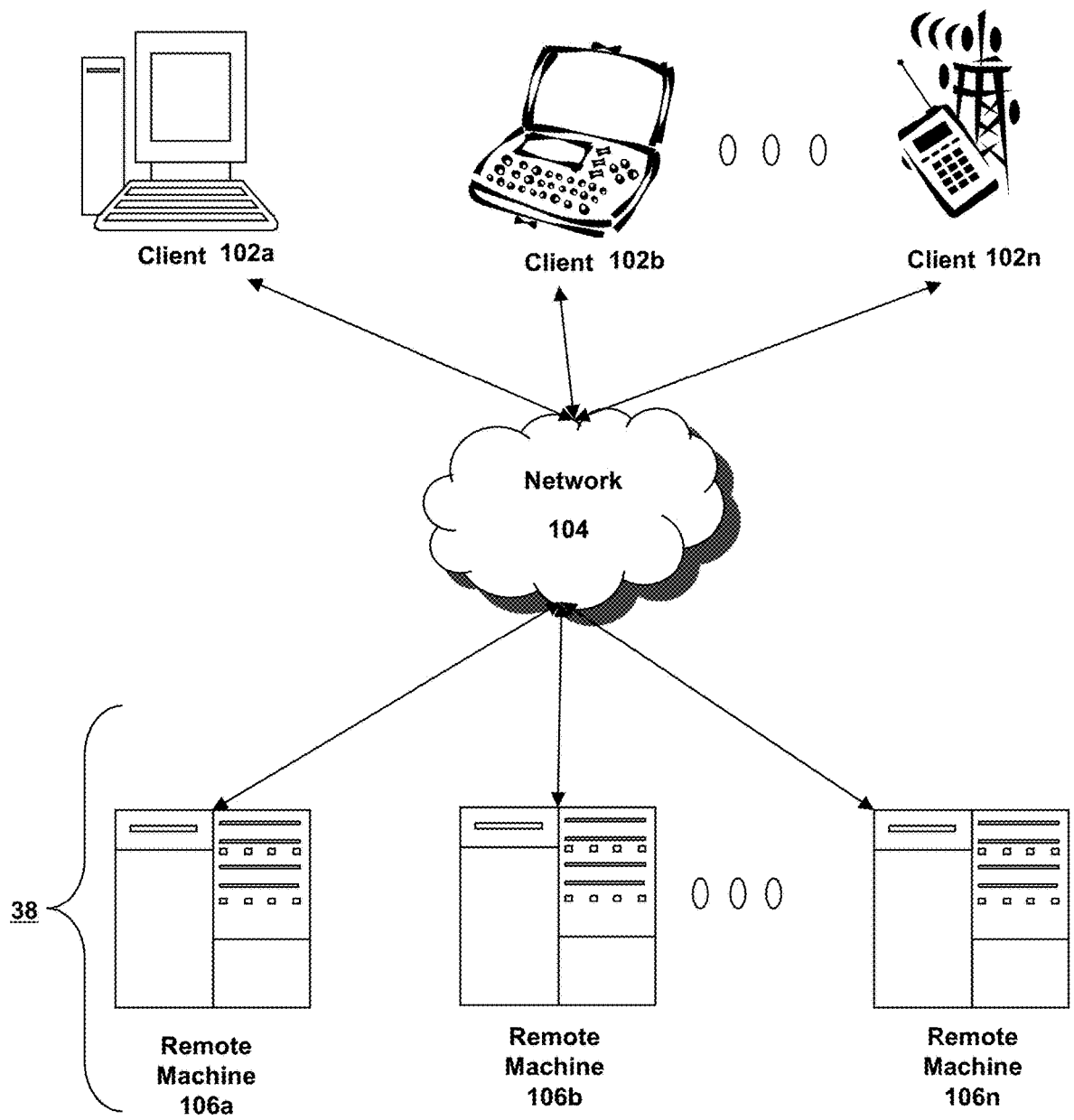
FIGS. 1A-1C are block diagrams depicting embodiments of computers useful in connection with the methods and systems described herein.

Referring now to FIG. 1A, an embodiment of a network environment is depicted. In brief overview, the network environment comprises one or more clients 102a-102n (also generally referred to as local machine(s) 102, client(s) 102, client node(s) 102, client machine(s) 102, client computer(s) 102, client device(s) 102, computing device(s) 102, endpoint(s) 102, or endpoint node(s) 102) in communication with one or more remote machines 106a-106n (also generally referred to as server(s) 106 or computing device(s) 106) via one or more networks 104.

Although FIG. 1A shows a network 104 between the clients 102 and the remote machines 106, the clients 102 and the remote machines 106 may be on the same network 104. The network 104 can be a local-area network (LAN), such as a company Intranet, a metropolitan area network (MAN), or a wide area network (WAN), such as the Internet or the World Wide Web. In some embodiments, there are multiple networks 104 between the clients 102 and the remote machines 106. In one of these embodiments, a network 104' (not shown) may be a private network and a network 104 may be a public network. In another of these embodiments, a network 104 may be a private network and a network 104' a public network. In still another embodiment, networks 104 and 104' may both be private networks.

The network 104 may be any type and/or form of network and may include any of the following: a point to point network, a broadcast network, a wide area network, a local area network, a telecommunications network, a data communication network, a computer network, an ATM (Asynchronous Transfer Mode) network, a SONET (Synchronous Optical Network) network, an SDH (Synchronous Digital Hierarchy) network, a wireless network, and a wireline network. In some embodiments, the network 104 may comprise a wireless link, such as an infrared channel or satellite band. The topology of the network 104 may be a bus, star, or ring network topology. The network 104 may be of any such network topology as known to those ordinarily skilled in the art capable of supporting the operations described herein. The network may comprise mobile telephone networks utilizing any protocol or protocols used to communicate among mobile devices, including AMPS, TDMA, CDMA, GSM, GPRS, or UMTS. In some embodiments, different types of data may be transmitted via different protocols. In other embodiments, the same types of data may be transmitted via different protocols.

A client 102 and a remote machine 106 (referred to generally as computing devices 100) can be any workstation, desktop computer, laptop or notebook computer, server, portable computer, mobile telephone or other portable telecommunication device, media playing device, a gaming system, mobile computing device, or any other type and/or form of computing, telecommunications or media device that is capable of communicating on any type and form of network and that has sufficient processor power and memory capacity to perform the operations described herein. A client 102 may execute, operate or otherwise provide an application, which can be any type and/or form of software, program, or executable instructions, including, without limitation, any type and/or form of web browser, web-based client, client-server application, an ActiveX control, or a JAVA applet, or any other type and/or form of executable instructions capable of executing on client 102.

In one embodiment, a computing device 106 provides functionality of a web server. In some embodiments, a web server 106 comprises an open-source web server, such as the APACHE servers maintained by the Apache Software Foundation of Delaware. In other embodiments, the web server executes proprietary software, such as the INTERNET INFORMATION SERVICES products provided by Microsoft Corporation of Redmond, Wash.; the ORACLE IPLANET web server products provided by Oracle Corporation of Redwood Shores, Calif.; or the BEA WEBLOGIC products provided by BEA Systems of Santa Clara, Calif.

In some embodiments, the system may include multiple, logically grouped, remote machines 106. In one of these embodiments, the logical group of remote machines may be referred to as a server farm 38. In another of these embodiments, the server farm 38 may be administered as a single entity.

Figure 1B:
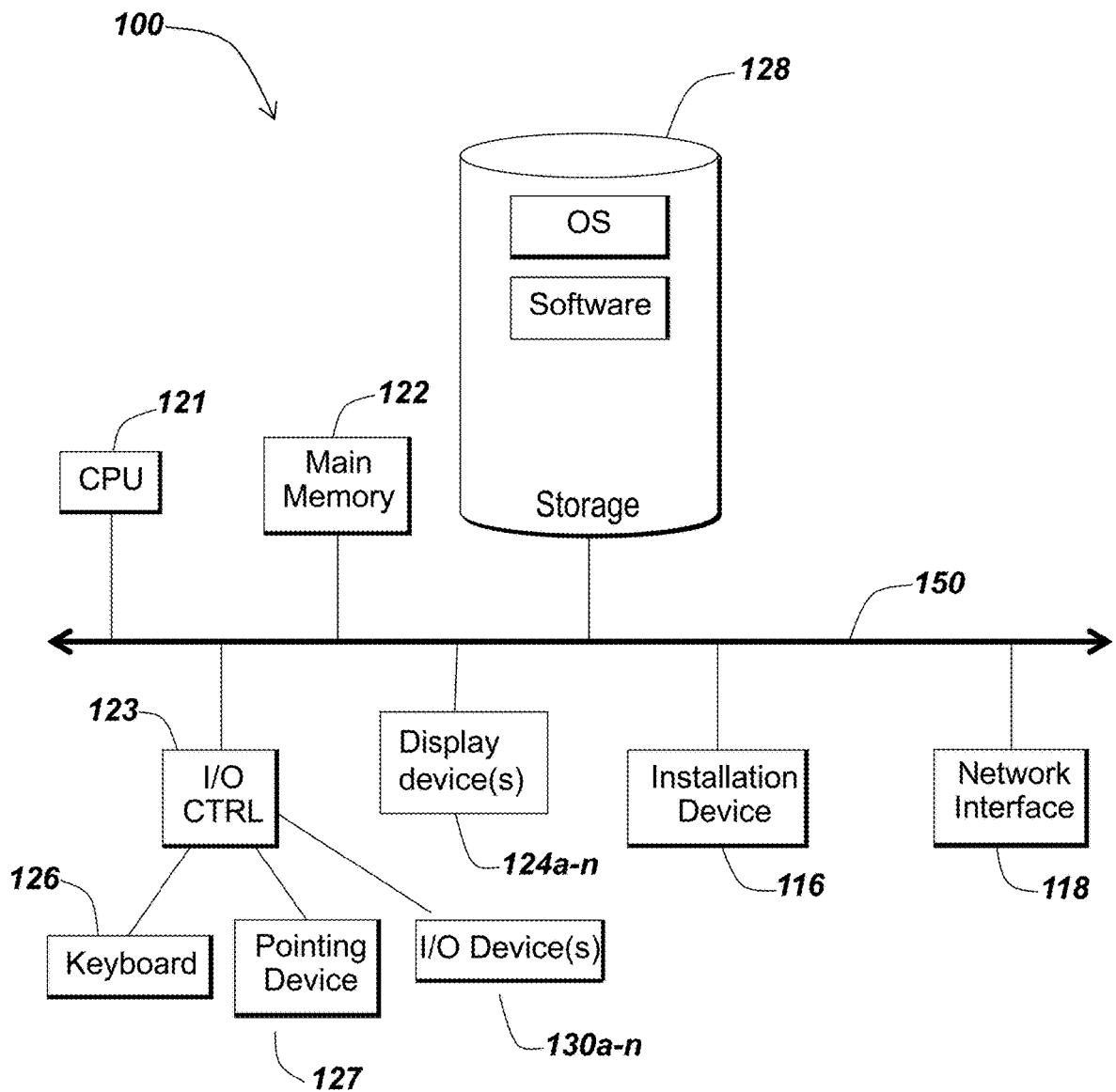
Figure 1C:
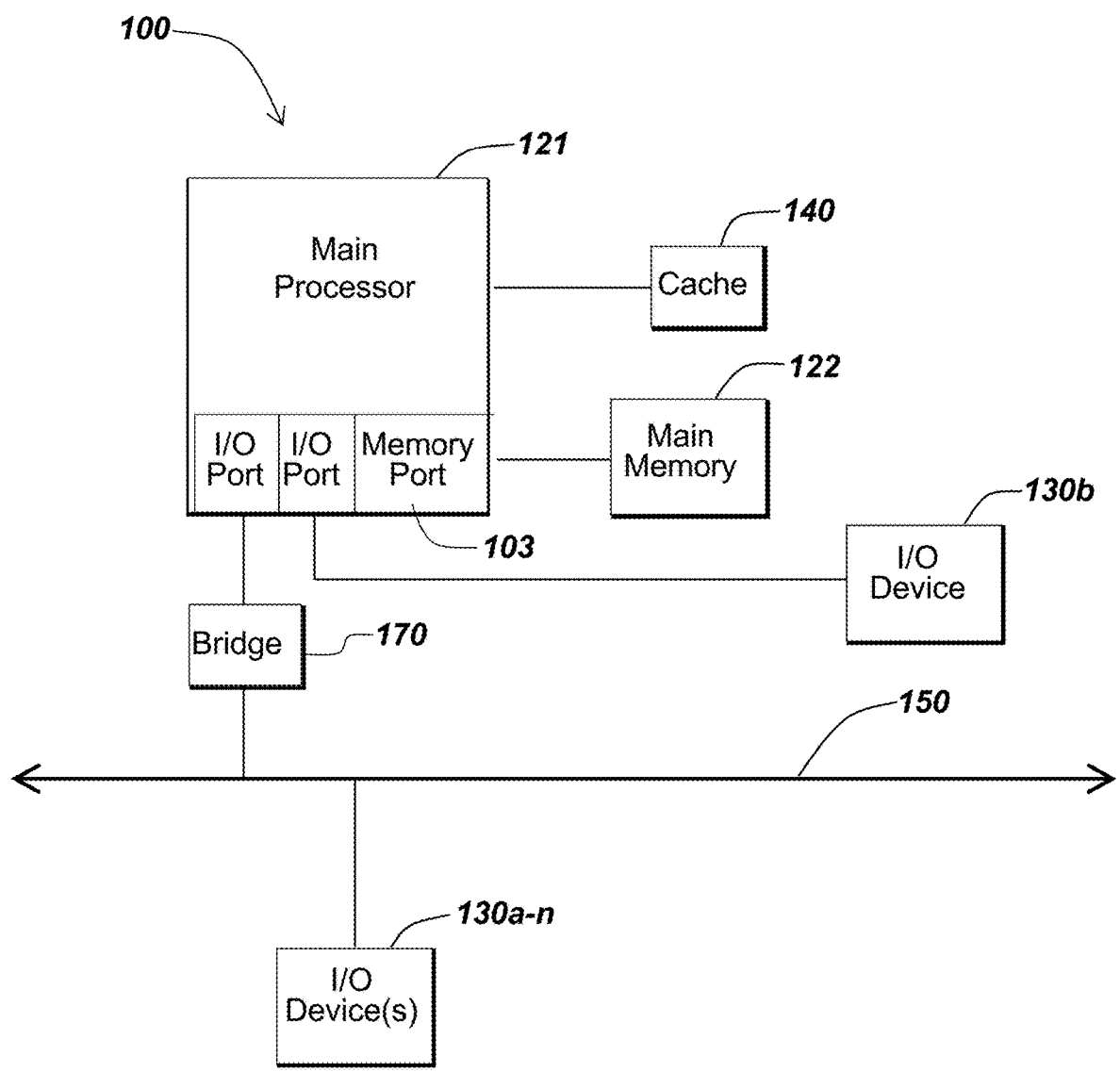

FIGS. 1B and 1C depict block diagrams of a computing device 100 useful for practicing an embodiment of the client 102 or a remote machine 106. As shown in FIGS. 1B and 1C, each computing device 100 includes a central processing unit 121, and a main memory unit 122. As shown in FIG. 1B, a computing device 100 may include a storage device 128, an installation device 116, a network interface 118, an I/O controller 123, display devices 124a-n, a keyboard 126, a pointing device 127, such as a mouse, and one or more other I/O devices 130a-n. The storage device 128 may include, without limitation, an operating system and software. As shown in FIG. 1C, each computing device 100 may also include additional optional elements, such as a memory port 103, a bridge 170, one or more input/output devices 130a-130n (generally referred to using reference numeral 130), and a cache memory 140 in communication with the central processing unit 121.

The central processing unit 121 is any logic circuitry that responds to and processes instructions fetched from the main memory unit 122. In many embodiments, the central processing unit 121 is provided by a microprocessor unit such as: those manufactured by Intel Corporation of Mountain View, Calif.; those manufactured by Motorola Corporation of Schaumburg, Ill.; those manufactured by Transmeta Corporation of Santa Clara, Calif.; those manufactured by International Business Machines of White Plains, N.Y.; or those manufactured by Advanced Micro Devices of Sunnyvale, Calif. The computing device 100 may be based on any of these processors, or any other processor capable of operating as described herein.

Main memory unit 122 may be one or more memory chips capable of storing data and allowing any storage location to be directly accessed by the microprocessor 121. The main memory 122 may be based on any available memory chips capable of operating as described herein. In the embodiment shown in FIG. 1B, the processor 121 communicates with main memory 122 via a system bus 150. FIG. 1C depicts an embodiment of a computing device 100 in which the processor communicates directly with main memory 122 via a memory port 103. FIG. 1C also depicts an embodiment in which the main processor 121 communicates directly with cache memory 140 via a secondary bus, sometimes referred to as a backside bus. In other embodiments, the main processor 121 communicates with cache memory 140 using the system bus 150.

In the embodiment shown in FIG. 1B, the processor 121 communicates with various I/O devices 130 via a local system bus 150. Various buses may be used to connect the central processing unit 121 to any of the I/O devices 130, including a VESA VL bus, an ISA bus, an EISA bus, a MicroChannel Architecture (MCA) bus, a PCI bus, a PCI-X bus, a PCI-Express bus, or a NuBus. For embodiments in which the I/O device is a video display 124, the processor 121 may use an Advanced Graphics Port (AGP) to communicate with the display 124. FIG. 1C depicts an embodiment of a computer 100 in which the main processor 121 also communicates directly with an I/O device 130b via, for example, HYPERTRANSPORT, RAPIDIO, or INFINIBAND communications technology.

A wide variety of I/O devices 130a-130n may be present in the computing device 100. Input devices include keyboards, mice, trackpads, trackballs, microphones, scanners, cameras, and drawing tablets. Output devices include video displays, speakers, inkjet printers, laser printers, and dyesublimation printers. The I/O devices may be controlled by an I/O controller 123 as shown in FIG. 1B. Furthermore, an I/O device may also provide storage and/or an installation medium 116 for the computing device 100. In some embodiments, the computing device 100 may provide USB connections (not shown) to receive handheld USB storage devices such as the USB Flash Drive line of devices manufactured by Twintech Industry, Inc. of Los Alamitos, Calif.

Referring still to FIG. 1B, the computing device 100 may support any suitable installation device 116, such as a floppy disk drive for receiving floppy disks such as 3.5-inch disks, 5.25-inch disks or ZIP disks, a CD-ROM drive, a CD-R/RW drive, a DVD-ROM drive, tape drives of various formats, USB device, hard drive or any other device suitable for installing software and programs. The computing device 100 may further comprise a storage device, such as one or more hard disk drives or redundant arrays of independent disks, for storing an operating system and other software.

Furthermore, the computing device 100 may include a network interface 118 to interface to the network 104 through a variety of connections including, but not limited to, standard telephone lines, LAN or WAN links (e.g., 802.11, T1, T3, 56 kb, X.25, SNA, DECNET), broadband connections (e.g., ISDN, Frame Relay, ATM, Gigabit Ethernet, Ethernet-over-SONET), wireless connections, or some combination of any or all of the above. Connections can be established using a variety of communication protocols (e.g., TCP/IP, IPX, SPX, NetBIOS, Ethernet, ARCNET, SONET, SDH, Fiber Distributed Data Interface (FDDI), RS232, IEEE 802.11, IEEE 802.11a, IEEE 802.11b, IEEE 802.11g, IEEE 802.11n, CDMA, GSM, WiMax, and direct asynchronous connections). In one embodiment, the computing device 100 communicates with other computing devices 100' via any type and/or form of gateway or tunneling protocol such as Secure Socket Layer (SSL) or Transport Layer Security (TLS). The network interface 118 may comprise a built-in network adapter, network interface card, PCMCIA network card, card bus network adapter, wireless network adapter, USB network adapter, modem, or any other device suitable for interfacing the computing device 100 to any type of network capable of communication and performing the operations described herein.

In some embodiments, the computing device 100 may comprise or be connected to multiple display devices 124a-124n, of which each may be of the same or different type and/or form. As such, any of the I/O devices 130a-130n and/or the I/O controller 123 may comprise any type and/or form of suitable hardware, software, or combination of hardware and software to support, enable or provide for the connection and use of multiple display devices 124a-124n by the computing device 100. One ordinarily skilled in the art will recognize and appreciate the various ways and embodiments that a computing device 100 may be configured to have multiple display devices 124a-124n.

In further embodiments, an I/O device 130 may be a bridge between the system bus 150 and an external communication bus, such as a USB bus, an Apple Desktop Bus, an RS-232 serial connection, a SCSI bus, a FireWire bus, a FireWire 800 bus, an Ethernet bus, an AppleTalk bus, a Gigabit Ethernet bus, an Asynchronous Transfer Mode bus, a HIPPI bus, a Super HIPPI bus, a SerialPlus bus, a SCI/LAMP bus, a FibreChannel bus, or a Serial Attached small computer system interface bus.

A computing device 100 of the sort depicted in FIGS. 1B and 1C typically operates under the control of operating systems, which control scheduling of tasks and access to system resources. The computing device 100 can be running any operating system such as any of the versions of the MICROSOFT WINDOWS operating systems, the different releases of the UNIX and LINUX operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 3.x, WINDOWS 95, WINDOWS 98, WINDOWS 2000, WINDOWS NT 3.51, WINDOWS NT 4.0, WINDOWS CE, WINDOWS XP, WINDOWS 7, and WINDOWS VISTA, all of which are manufactured by Microsoft Corporation of Redmond, Wash.; MAC OS manufactured by Apple Inc. of Cupertino, Calif.; OS/2 manufactured by International Business Machines of Armonk, N.Y.; and LINUX, a freely-available operating system distributed by Caldera Corp. of Salt Lake City, Utah, or any type and/or form of a UNIX operating system, among others.

The computing device 100 can be any workstation, desktop computer, laptop or notebook computer, server, portable computer, mobile telephone or other portable telecommunication device, media playing device, a gaming system, mobile computing device, or any other type and/or form of computing, telecommunications or media device that is capable of communication and that has sufficient processor power and memory capacity to perform the operations described herein. In some embodiments, the computing device 100 may have different processors, operating systems, and input devices consistent with the device. In other embodiments, the computing device 100 is a mobile device, such as a JAVA-enabled cellular telephone or personal digital assistant (PDA). The computing device 100 may be a mobile device such as those manufactured, by way of example and without limitation, by Motorola Corp. of Schaumburg, Ill.; Kyocera of Kyoto, Japan; Samsung Electronics Co., Ltd., of Seoul, Korea; Nokia of Finland; Hewlett-Packard Development Company, L.P. and/or Palm, Inc., of Sunnyvale, Calif.; Sony Ericsson Mobile Communications AB of Lund, Sweden; or Research In Motion Limited, of Waterloo, Ontario, Canada. In yet other embodiments, the computing device 100 is a smart phone, POCKET PC, POCKET PC PHONE, or other portable mobile device supporting Microsoft Windows Mobile Software.

In some embodiments, the computing device 100 is a digital audio player. In one of these embodiments, the computing device 100 is a digital audio player such as the Apple IPOD, IPOD Touch, IPOD NANO, and IPOD SHUFFLE lines of devices, manufactured by Apple Inc. of Cupertino, Calif. In another of these embodiments, the digital audio player may function as both a portable media player and as a mass storage device. In other embodiments, the computing device 100 is a digital audio player such as those manufactured by, for example, and without limitation, Samsung Electronics America of Ridgefield Park, N.J.; Motorola Inc. of Schaumburg, Ill.; or Creative Technologies Ltd. of Singapore. In yet other embodiments, the computing device 100 is a portable media player or digital audio player supporting file formats including, but not limited to, MP3, WAV, M4A/AAC, WMA Protected AAC, AEFF, Audible audiobook, Apple Lossless audio file formats and .mov, .m4v, and .mp4 MPEG-4 (H.264/MPEG-4 AVC) video file formats.

In some embodiments, the computing device 100 comprises a combination of devices, such as a mobile phone combined with a digital audio player or portable media player. In one of these embodiments, the computing device 100 is a device in the Motorola line of combination digital audio players and mobile phones. In another of these embodiments, the computing device 100 is a device in the IPHONE smartphone line of devices manufactured by Apple Inc. of Cupertino, Calif. In still another of these embodiments, the computing device 100 is a device executing the ANDROID open source mobile phone platform distributed by the Open Handset Alliance; for example, the device 100 may be a device such as those provided by Samsung Electronics of Seoul, Korea, or HTC Headquarters of Taiwan, R.O.C. In other embodiments, the computing device 100 is a tablet device such as, for example and without limitation, the IPAD line of devices manufactured by Apple Inc.; the PLAYBOOK manufactured by Research In Motion; the CRUZ line of devices manufactured by Velocity Micro, Inc. of Richmond, Va.; the FOLIO and THRIVE line of devices manufactured by Toshiba America Information Systems, Inc. of Irvine, Calif.: the GALAXY line of devices manufactured by Samsung; the HP SLATE line of devices manufactured by Hewlett-Packard; and the STREAK line of devices manufactured by Dell, Inc. of Round Rock, Tex.

In one aspect, the methods and systems disclosed herein provide functionality for extracting information from audio streams generated based on user utterances and for identifying parameters within the extracted information that may be used to generate a search query. Implementation of such functionality may result in improved search results; for example, and without limitation, in finding the best provider for a patient seeking a referral.

The methods and systems described herein may also provide functionality for automatically modifying a user interface in real time, during a phone call to a call center, to provide a display of additional data to an operator at the call center. In some embodiments, the disclosed methods and systems receive in-call data when a patient calls a call center with a particular need, and the methods and systems described herein provide an operator receiving the call with potential referral information necessary to aid the patient in scheduling an appointment. The system may furnish the operator with materials necessary to determine the needs of a patient (e.g., through generation or modification of a user interface display to include new data); for example, and without limitation, the system may identify a physician referral that will match at least one (potentially as-yet unspecified but inferred) requirement of the patient. As another example, the system may allow the operator to assist a patient that is unable or unwilling to express herself fully. As a further example, the system may provide the operator with a context in which to understand a patient situation without having to explicitly ask the patient all the questions required to understand the context. In some embodiments, the system and method use the richness of physician profiles as described herein to find an ideal match for the needs of the patient in a dynamic, flexible, and rapid manner.

In other embodiments, the disclosed methods and systems receive audio streams generated when a patient interacts with a voice interface application (e.g., applications such as SIRI provided by Apple Inc., or ALEXA provided by Amazon.com Inc.) to access and interact with an application. By way of example, a patient may utter a command to interact with an application offered by a healthcare or health-related organization (including, without limitation, a doctor's office or an insurance company); the application may be executed on the patient's computing device (e.g., a mobile app provided by a doctor's office, downloaded by the patient, and executed on the patient's mobile phone) or on another machine and accessed via a computer network communications channel (e.g., connecting over a network 104 using a web browser application executed on the patient's computing device to access an application provided by a computing device of the doctor's office, in which case, an audio stream generated based on the patient utterances may be converted to text locally or at a remote machine and the converted text may be transmitted to the system 200 for analysis).

Figure 2A:
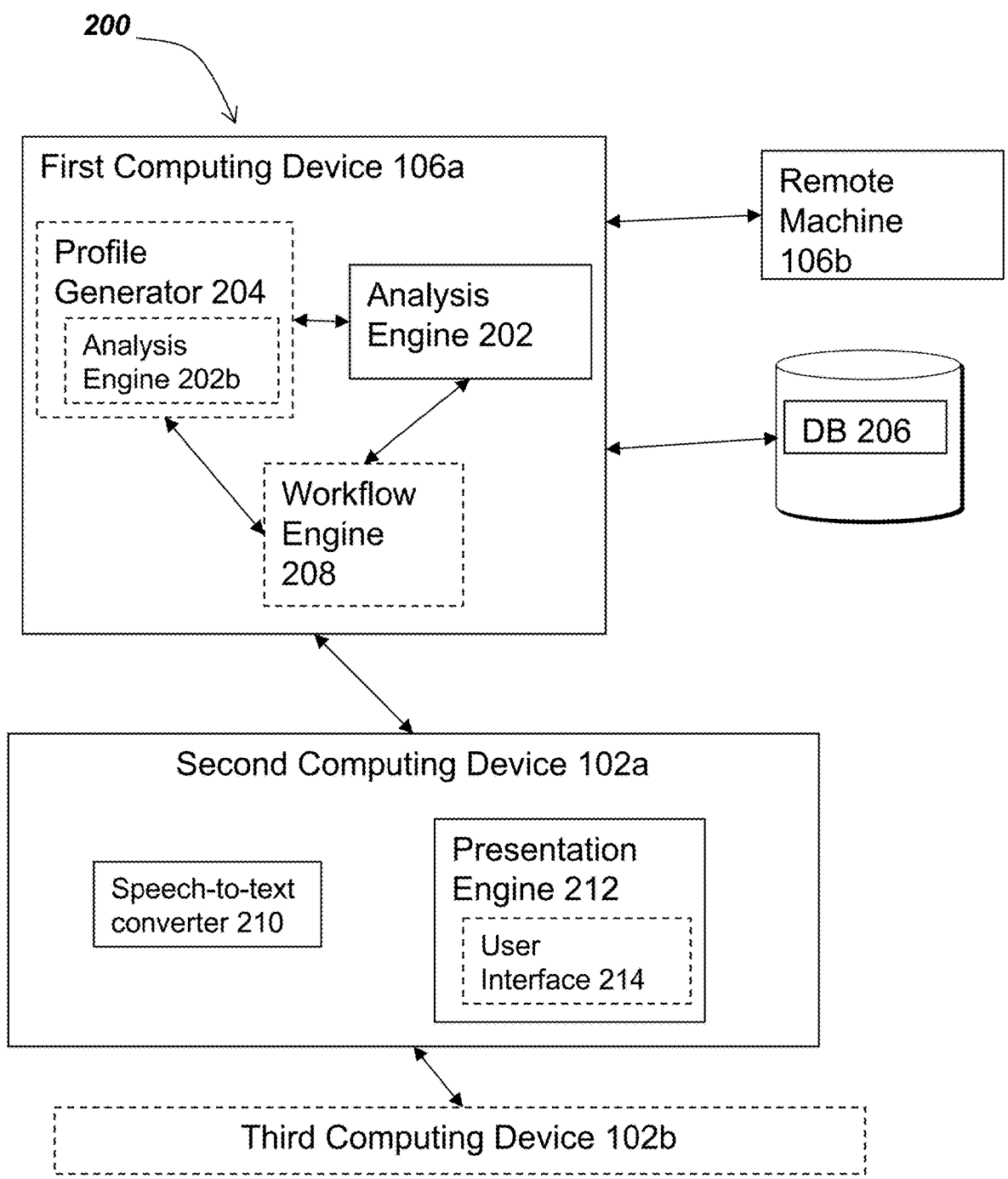
FIG. 2A is a block diagram depicting one embodiment of a system for analyzing speech to generate a potential referral.

Referring now to FIG. 2A, a block diagram depicts one embodiment of a system 200 for analyzing speech to generate a potential referral. In brief overview, the system 200 includes a first computing device 106a, an analysis engine 202, and a second computing device 102.

Referring to FIG. 2A in further detail, the system 200 includes a first computing device 106a. In some embodiments, the first computing device 106a is a computing device 100 as described above in reference to FIGS. 1A-1C. The first computing device 106a may be a remote machine 106a as described above in reference to FIGS. 1A-1C. The first computing device 106a may function as a server, as described above in reference to FIGS. 1A-1C. The first computing device 106a may function as a client device, as described above in reference to FIGS. 1A-1C. The first computing device 106a may be a plurality of computing devices 100, as described above in reference to FIGS. 1A-1C, working in concert as a single device.

In some embodiments, the analysis engine 202 is provided as part of a software application operating on the first computing device 106a. In some embodiments, the analysis engine 202 analyzes data generated during a call by a patient to a call center (e.g., voice data converted into a computer-processable format), the data received from the second computing device 102, identifies patient data associated with the patient, responsive to the analysis, determines at least one requirement of the patient based upon the identified patient data and the analysis, generates a potential referral to a physician for the patient, the physician having a profile that satisfies the determined at least one requirement, and provides, to the call center, the potential referral during the call, as set forth in further detail below.

Although referred to herein as "calls," "telephone calls," or "phone calls," it should be understood that any means of exchanging audio and/or video data by the patient and the call center operator may constitute a "call," including a communications session placed via softphone, Voice Over Internet Protocol (VOIP)-based applications on physical telephones or software applications, video conferencing applications, or other telecommunications platforms. By way of example, in addition to or instead of interacting with the system 200 by speaking to an agent on a phone (or other voice channel), a patient may interact with the system 200 via a voice interface application (e.g., SIRI, ALEXA, etc.), with the help of an agent.

The system 200 may create the physician profile. In some embodiments, the profile includes at least one identification of a professional connection of the physician. In other embodiments, the profile includes at least one lifestyle characteristic of the physician. The profile may also include areas of expertise belonging to the physician. The physician may be any kind of doctor, a medical student, a nurse, a pharmacist, or any type of healthcare professional or assistant to a professional. In another embodiment, the referral is to another individual working in a professional services environment such as, without limitations, a lawyer, a consultant, real estate professional, or financial services professional (e.g., accountants and bankers). In still another embodiment, professionals include students (of any discipline), education professionals (teachers, school administrators, etc.), athletes, and politicians.

The system 200 may include a profile generator 204. The profile generator 204 may be provided as part of a software application operating on the first computing device 106a; in other embodiments, the profile generator 204 executes on another computing device (not shown). In some embodiments, the profile generator 204 automatically generates a profile of at least one physician. In one embodiment, the profile generator 204 accesses a database 206 to retrieve data associated with the physician for inclusion in the profile. In another embodiment, the profile generator 204 accesses a second remote computing device 106b to retrieve data associated with the physician; for example, the profile generator 204 may query a remotely located database or computer. In still another embodiment, the profile generator 204 accesses a second remote computing device 106b to identify a physician for whom to generate a profile. The remote computing device 106b may be owned, operated, or otherwise associated with an entity unaffiliated with the entity implementing the methods and systems described herein.

In some embodiments, the profile generator 204 includes a second analysis engine 202b (depicted in shadow in FIG. 2A). In one of these embodiments, the second analysis engine 202b analyzes data retrieved by the profile generator 204. In another of these embodiments, the second analysis engine 202b determines whether to include the analyzed data in the generated profile. In one example, the second analysis engine 202b may include the functionality of the analysis engine 202. In another example, the second analysis engine 202b is a version of the analysis engine 202 that has been customized to include functionality for determining whether to include data in a generated profile. In other embodiments, the profile generator 204 is in communication with a second analysis engine 202b. In further embodiments, the profile generator 204 accesses the analysis engine 202, which makes a determination as to whether to include data in a generated profile.

In some embodiments, the profile generator 204 stores a generated profile in a database 206. In some embodiments, the database 206 is an ODBC-compliant database. For example, the database 206 may be provided as an ORACLE database, manufactured by Oracle Corporation of Redwood Shores, Calif. In other embodiments, the database 206 can be a Microsoft ACCESS database or a Microsoft SQL server database, manufactured by Microsoft Corporation of Redmond, Wash. In still other embodiments, the database 206 may be a custom-designed database based on an open source database, such as the MYSQL family of freely available database products distributed by MySQL AB Corporation of Uppsala, Sweden. In some embodiments, the database 206 is maintained by, or associated with, a third party.

In some embodiments, the profile generator 204 additionally generates a profile for an entire organization; for example, in addition to profiling a professional, such as the physician, the system may generate profiles for companies, academic institutions, professional associations, or other entities. In one of these embodiments, the analysis engine 202 analyzes profiles for individuals within the organization to develop a profile for the organization as a whole. In another of these embodiments, the analysis engine 202 analyzes the organizational profile to generate a level of expertise of the organization. By way of example, a teaching hospital hiring highly qualified doctors and renowned for its work in a particular medical specialty may have a high level of expertise in that industry; such a level of expertise would be relevant to, for example, a medical student seeking to work in the medical specialty, a medical device company seeking to receive the perspective of reputable doctors on a new device, or a patient seeking a certain level of expertise from his or her doctor. In other embodiments, the profile generator 204 generates a profile for an organization independent of generating a profile for any individual professional affiliated with the organization (e.g., by generating a profile for a hospital without generating profiles for individual employees of the hospital).

In one embodiment, the profile generator 204 generates an initial profile of either the professional or the entity automatically and without any input from the professional or entity. In such an embodiment, the profile generator 204 generates the profile without the professional requesting the generation of the profile and without the professional or entity providing any information to the system. In another embodiment, the profile generator 204 may receive input from the professional or the entity modifying the automatically generated profile; for example, the remote machine 106 may execute a web server displaying a web page from which the professional or an individual associated with the entity can make modifications to the profile after the profile generator 204 generates the profile.

Figure 2B:
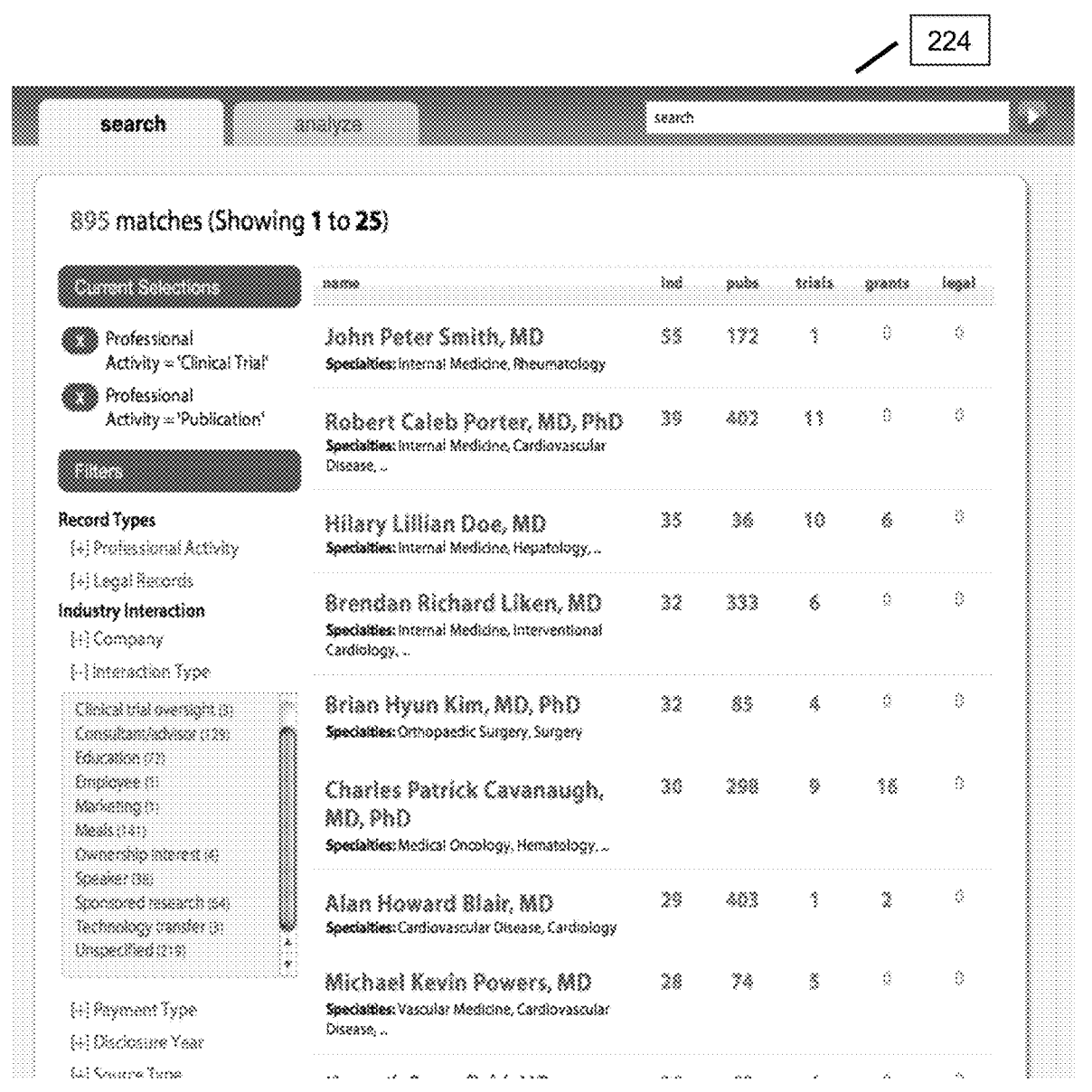

Referring to FIG. 2B, a screen shot depicts one embodiment of profiles generated by the profile generator 204. In one embodiment, a user interface 224 displays a listing of profiled professionals. As shown in FIG. 2B, by way of example, a listing of a profiled professional may include a summary of the professional's specialties, a number of publications by the professional, a number of grants, and a number of trials participated in. As shown in FIG. 2B, the user interface 224 may provide functionality allowing users to search for profiled professionals.

In one embodiment, the profile generator 204 accesses local and remote databases to automatically generate the profile. In another embodiment, the profile generator 204 identifies connections the physician has to other professionals or entities—including, for example, co-workers, employers, employees, mentors, mentees, colleagues, co-authors, co-presenters, and vendors. For example, the profile generator 204 may search, without limitation, databases of publications (e.g., journal databases), hospital databases (e.g., to find out where a doctor works), databases of current and former academic faculty (e.g., to find out where someone taught or teaches, or which professors a professional studied under), social media databases, databases of sports club or gym memberships, and databases of alumni (e.g., to determine where the professional went to school). In still another embodiment, the profile generator 204 may search databases including, without limitation, databases storing information relating to demographics, professional writing (publications, etc.), and disciplinary, legal, medical, economic, and credentialing information. In some embodiments, the profile generator 204 accesses primary data. In other embodiments, the profile generator 204 accesses secondary data. In still other embodiments, the profile generator 204 accesses some data directly and some data indirectly, for example, by inferring information or relationships from other data (i.e., inferring the existence of mentoring relationships). In further embodiments, the profile generator 204 accesses user-generated data. In some embodiments, the profile generator 204 accesses publicly available information. In other embodiments, the profile generator 204 accesses proprietary databases.

In some embodiments, the profile generator 204 accesses data including, without limitation, a level of education, an affiliation with an educational institution, a type of profession, an area of specialization within a profession, an identification of a professor, an identification of a mentor, an identification of an employer, publications, presentations, professional affiliations, memberships, types of clients, office buildings, an identification of a colleague, an identification of a geographical area within which the professional works or lives, biographical information, and areas of expertise; data not explicitly associated with a professional attribute of the professional may be referred to as a lifestyle characteristic. In some embodiments, the profile generator 204 accesses user-generated data. In other embodiments, the profile generator 204 accesses interaction data such as what drugs physicians prescribed, what procedures they followed, to whom they refer patients or colleagues, preferences as to brand, and lifecycle data.

In some embodiments, the profile generator 204 analyzes accessed data to determine whether to include the accessed data in a profile. In other embodiments, the profile generator 204 determines whether accessed data is duplicative of data already in the profile. For example, the profile generator 204 may perform entity resolution (e.g., determining that "Doctor J. Reynolds" is the same individual as "Jonathan Reynolds, MD"). In one of these embodiments, the profile generator 204 determines whether accessed data indicates that data already in the profile is no longer current (e.g., obsolete) or has been modified over time. In further embodiments, the profile generator 204 may identify data to include in a profile using a chain of inference. For example, analyzing a professional's name associated with a publication in a well-regarded journal may allow the profile generator 204 to determine that the professional has a particular area of domain expertise; the area of domain expertise and the professional's name may allow the profile generator 204 to perform a search of a database providing additional data relating to the professional (e.g., a license number, membership, employer, or other data). As one of ordinary skill in the art will understand, having accessed one or more types of data, the profile generator 204 generates the profile by including one or more versions of the accessed data in a data structure, including, without limitation, placing copies, summaries, representations, identifications of, links to, or versions of the accessed data in the profile.

In some embodiments, the profile generator 204 is not dependent upon self-entry of data. In other embodiments, the profile generator 204 accesses passively collected data to generate a profile. In one of these embodiments, the profiled physician is not aware of the data collection process. In another of these embodiments, the profile generator 204 accesses administrative or clinical systems to generate a profile. By way of example, and without limitation, administrative systems may include billing, operational, or human resources systems. As another example, and without limitation, clinical systems may include electronic medical record systems or case registries.

In one embodiment, the profile generator 204 generates a profile for a professional; for example, and without limitation, the profile generator 204 may generate a profile of a physician. In another embodiment, the profile generator 204 also generates a profile for a provider of a good or service; the profile generator 204 may generate a profile for a diverse set of providers including, by way of example and without limitation, a provider such as a medical device company, a pharmaceutical company, a professional services company, or individuals employed by such companies. In still another embodiment, the profile generator 204 generates an institutional profile. For example, as indicated above, the profile generator 204 may generate a profile for a company, which may include entities of varied corporate structures (for-profit, not-for-profit, non-profit, and charitable organizations generally). In yet another embodiment, the profile generator 204 generates a profile of an opportunity. For example, the profile generator 204 may generate a profile for an opportunity such as a job opportunity (e.g., a potential client looking to hire a professional, an opportunity in a particular industry such as a consulting or speaking opportunity, or an opportunity with an entity seeking to hire a professional on a contract, full-time, or part-time basis).

In one embodiment, the profile generator 204 uses the generated profile to generate a second profile. For example, in generating an entity's profile, the profile generator 204 may incorporate data from profiles associated with employees of an entity associated with the physician, such as the entity employing the physician. As another example, in generating an individual's profile, the profile generator 204 may incorporate data from profiles associated with direct reports, mentees, mentors, or other profiled individuals. In some embodiments, therefore, the profile includes at least one identification of a professional connection of the profiled physician. In other embodiments, the profile includes at least one identification of a lifestyle characteristic of a profiled physician (e.g., of memberships, hobbies, activities, travel preferences, or other characteristics that may not be related to the individual's profession).

In some embodiments, the profile generator 204 dynamically updates the profile to reflect changes to the data underlying the profile. The profile may include information that is likely to change frequently or continuously; such information may be referred to as a dynamic attribute. The information may include the availability of the profiled physician. For instance, the date, time, location, or type of appointment that can be scheduled may change every time the physician modifies her schedule or has a new entry added to the schedule by an automated process as described in further detail below. Likewise, the availability of additional resources relevant to a particular type of appointment, such as additional personnel or special equipment, may change each time the profiled physician or other providers schedule the use of the additional personnel or special equipment; the availability of equipment may be further affected by scheduled maintenance, unexpected repairs, or the need to replace non-reusable components of the equipment.

As an additional example, where the profile of a physician includes clinical fluency data as set forth in further detail below, information concerning the recent activity of the physician, such as how many times the professional has completed a particular kind of procedure recently, may continuously change. Similarly, the schedule load of the physician, or how many times the physician has been scheduled to perform a particular procedure in the near future, may change dynamically as the result of scheduling activity. In some embodiments, a medical provider's appropriateness to see patients with certain conditions may change over time; for instance, the analysis engine 202 may determine that a physician is unable to see a patient having a particular condition due to a change in clinical fluency or patient outcome information. The physician may be unable to accept new patients owing to the schedule flexibility necessary to attend to current patients. In other embodiments, financial constraints, such as the coverage of a particular procedure by a particular insurance carrier, may change.

In some embodiments, the profile generator 204 updates dynamically changing data in the profile by querying and analyzing data from a plurality of sources of information. In one of these embodiments, keeping profile data updated allows the system to use gathered data effectively when seeking optimal matches satisfying multiple constraints. However, each of the plurality of sources may have one or more constraints or limitations that the system needs to consider when balancing the accuracy and timeliness of the dynamic attributes. Examples of limitations include an ability to acquire large amounts of data quickly (e.g., retrieving a year's worth of scheduling data for each of thousands of providers may take several hours on some systems), a level of completeness of the data (e.g., whether provider scheduling data is reported to the information source being polled), and a type of identifier used by each information source (e.g., information from different systems may not identify a profiled physician using the same identifier, or key). Therefore, the profile generator 204 may select a particular technique to form a particular query based upon characteristics of one or more of the plurality of information sources. By way of example, and without limitation, the profile generator 204 may determine to download and update a set of information for all or a majority of professionals at one time (e.g., nightly updates), may determine to download and update a set of information for a subset of professionals at a second time (e.g., hourly updates for professionals who exhibit a high frequency of modifications to associated scheduling data), and may determine to subscribe to a notification system and update profile data as soon as a notification of a change is received (e.g., accept a Health Level 7 (HL7) feed from a scheduling system to receive booking and cancelation notifications).

As an additional example, the profile generator 204 may use frequent queries or a continuous feed to receive immediate updates concerning the schedule of each physician over a short term, such as days or weeks, while using a nightly batch to retrieve longer term schedule information, such as each medical provider's schedule over the ensuing year. The profile generator 204 may select the query approach to use when updating a particular kind of data based on the speed with which that kind of data has updated in the past; for instance, if the availability of a particular physician tends to change slowly, the profile generator 204 may cease frequent queries or feed subscriptions concerning that physician's availability, and rely instead on updates to the availability data in a nightly batch. The profile generator 204 may similarly use stored rules based on the likely behavior of different categories of data to govern the approach used in updating each category of data; the profile generator 204 may modify such rules based on the historical behavior of data as described above.

In other embodiments, a particular data source may have a tendency to make erroneous updates to its data; the profile generator 204 may respond by comparing the data from two consecutive queries to detect and eliminate errors. Likewise, a particular data source may tend to have incomplete data, owing to irregular updates to that data, or a lack of compliance with reporting protocols by staff associated with that data source; as a result, the profile generator 204 may flag the data from that source in a profile as potentially incomplete or out-of-date.

In some embodiments, the use of multiple categories of data concerning a physician to determine skill sets, areas of expertise, and levels of expertise produces an unexpected increase in accuracy for predictions of performance by the profiled physician. Because the analysis of a greater volume of collected data can rely not only on the additional data, but also on the interactions of the additional data with other collected data, the degree of accuracy of the profile may increase faster than a linear function of the additional data collection. The variability of sources of collected data and continued collection of the data over time may enhance that accuracy further.

In some embodiments, the profile generator 204 dynamically updates the profile in response to the creation of a new referral to the profiled physician. In some embodiments, the profile generator 204 receives the indication from the referring professional via the second computing device 102. The profile generator 204 may provide a user interface 224, such as a web page, by means of which the referring professional may indicate that he or she has made the referral choice. In some embodiments, the profile generator 204 receives an indication that the referring professional has made the referral from a remote device 106b; for example, and without limitation, a remote device 106b associated with the referred professional may transmit the indication to the profile generator 204.

The profile generator 204 may update the profile of the physician responsive to the received indication. In some embodiments, the profile generator 204 updates a level of expertise of the physician in an industry. For instance, the profile generator 204 may increase the level of expertise of the physician in general each time the first computing device 106a receives a referral from a referring physician. The profile generator 204 may increase the level of expertise of the physician in a particular field each time the first computing device 106a receives a referral from a referring physician. In some embodiments, the profile generator 204 updates the level of expertise by receiving data describing the outcome of the referral, and updating the level of expertise to reflect that data. For example, and without limitation, the profile generator 204 may receive data indicating the clinical outcome of the referral. The profile generator 204 may receive patient feedback concerning the referral. The profile generator 204 may receive feedback concerning the referral from the employer of the physician. In some embodiments, the profile generator 204 receives feedback from a referring physician. The profile generator 204 may receive information concerning the outcome of the referral from the physician to whom the referral was given.

In some embodiments, the profile generator 204 modifies a category of expertise of the physician. The profile generator 204 may determine that the referral concerns a particular category of expertise. The referral may explicitly indicate the category of expertise to which it pertains. The analysis engine 202 may determine that the referral implicitly describes a category of expertise that concerns the referral. In some embodiments, the analysis engine 202 associates a procedure requested in the referral with a category of expertise. In some embodiments, the analysis engine 202 associates a diagnosis requested in the referral with a category of expertise. In some embodiments, the profile generator 204 adds a new category of expertise to the profile of the physician. In some embodiments, the profile generator 204 increases the level of expertise of the physician in a category of expertise associated with the referral.

In some embodiments, the analysis engine 202 analyzes the generated profile and determines, responsive to the analysis, a level of expertise of a professional in an industry. In some embodiments, a profiled individual or entity has a level of domain expertise. In some embodiments, a level of expertise refers to a level of familiarity with a particular subject. The analysis engine 202 may determine, responsive to the analysis, a category of expertise, in some embodiments, as set forth more fully below. In other embodiments, the analysis engine 202 determines a level of influence. For example, the analysis engine 202 may determine that a profiled individual or entity has a level of influence over one or more other individuals or entities based, at least in part, on the level of expertise the profiled individual or entity has in a particular industry or domain. In one embodiment, a level of expertise refers to one or more internal factors—factors specific to, or internal to, a profiled physician—while a level of influence refers to one or more external factors—factors independent of the physician and relating to the physician's interactions with others. Examples of factors considered in establishing levels of expertise include numbers of articles, numbers of grants, levels of involvement in particular organizations and a number of organizations with which the individual interacts (e.g., a number of interactions an academic has with a professional in industry or vice versa). Examples of factors considered in establishing levels of influence include external factors associated with a profiled physician, such as a reporting structure relative to another professional or a professional connection such as a mentoring, training or other connection between the profiled physician and a second professional. In other embodiments, a level of influence refers to a degree of reach of a physician or for how long the physician influences others' behaviors. In further embodiments, the analysis engine 202 determines both a level of expertise and a level of influence. The analysis engine 202 transmits, to a second computing device, an identification of the determined level of expertise.

The analysis engine 202 may analyze a generated profile, and determine, responsive to the analysis, a level of expertise of the physician in an industry. In one embodiment, the analysis engine 202 includes functionality for retrieving stored profiles from a database 206. In another embodiment, the analysis engine 202 includes functionality for requesting profiles and receiving profiles from the profile generator 204. In still another embodiment, the analysis engine 202 includes functionality for accessing previously analyzed profiles for comparison with a generated profile. In an additional embodiment, the analysis engine 202 includes functionality for accessing payroll records pertaining to the services of the physician who is the subject of the profile. The analysis engine 202 may receive the payroll records from a remote machine 106b; for example, a remote machine 106b that maintains payroll records for an institution at which the professional works. In other embodiments, the analysis engine 202 includes functionality for accessing billing records pertaining to the services of the physician who is the subject of the profile. The analysis engine 202 may receive the billing records from a remote machine 106b; for example, a remote machine 106b that maintains billing records for an institution at which the professional works. The analysis engine 202 may also include functionality for receiving electronic medical records; in some embodiments, the analysis engine 202 receives electronic medical records from a remote machine 106b that maintains such records.

In one embodiment, the analysis engine 202 analyzes the generated profile to identify characteristics indicative of a level of expertise. In some embodiments, the analysis engine 202 analyzes the generated profile to identify characteristics indicative of a level of influence, which, in one of these embodiments, includes a degree of reach of a physician or for how many others the physician has a level of influence or for how long the physician influences others' behaviors. In some embodiments, drivers of influence include publications, grants, patents, referral volume, number of years of experience, degrees of risk, degrees of compliance, and tenure at particular hospitals. In other embodiments, levels of expertise are factors internal to the profiled professional, such as, without limitation, publications, grants, and experience; levels of influence may be factors external to the profiled professional, such as reporting structure or training structure.

In one embodiment, the analysis engine 202 analyzes a network of professionals to which the profiled professional belongs. The analysis engine 202 may identify ways in which the profiled professional stands out from peers in the network of professionals. The analysis engine 202 may identify characteristics that the profiled professional has in common with peers in the network of professionals. The analysis engine 202 may identify professionals in the network who are farther along in their careers than the profiled professional and compare and contrast the two. In some embodiments, the analysis engine 202 may analyze any or all of the data accessed by the profile generator 204 including, but not limited to, information listed above in connection with FIG. 2.

In some embodiments, the analysis engine 202 determines, responsive to the analysis, a level of expertise in an industry of the at least one of the professional and the entity. The analysis engine 202 may, for example, determine that a publication generated by the profiled professional is accessed by a majority of the members of his or her professional network or by influential members of the industry. In some embodiments, the level is provided as a descriptive term or phrase. In other embodiments, the level is provided as a binary value (e.g., "expert" or "not an expert"). In further embodiments, however, the level is not provided as a binary value but as a range based upon—and varying based upon—one or more weights. For example, the analysis engine 202 may be configured to weight certain types of profile data more or less heavily than others and to combine the various weights of various profile data to generate a level of expertise; in generating a profile of a researcher, for example and without limitation, the analysis engine 202 may count a recent publication in a prestigious journal as worth 0.7 points, while only weighing employment with a second tier institution as 0.2 and then combine the two to generate an overall level of expertise as 0.9 (e.g., out of 1.0).

Figure 2C:
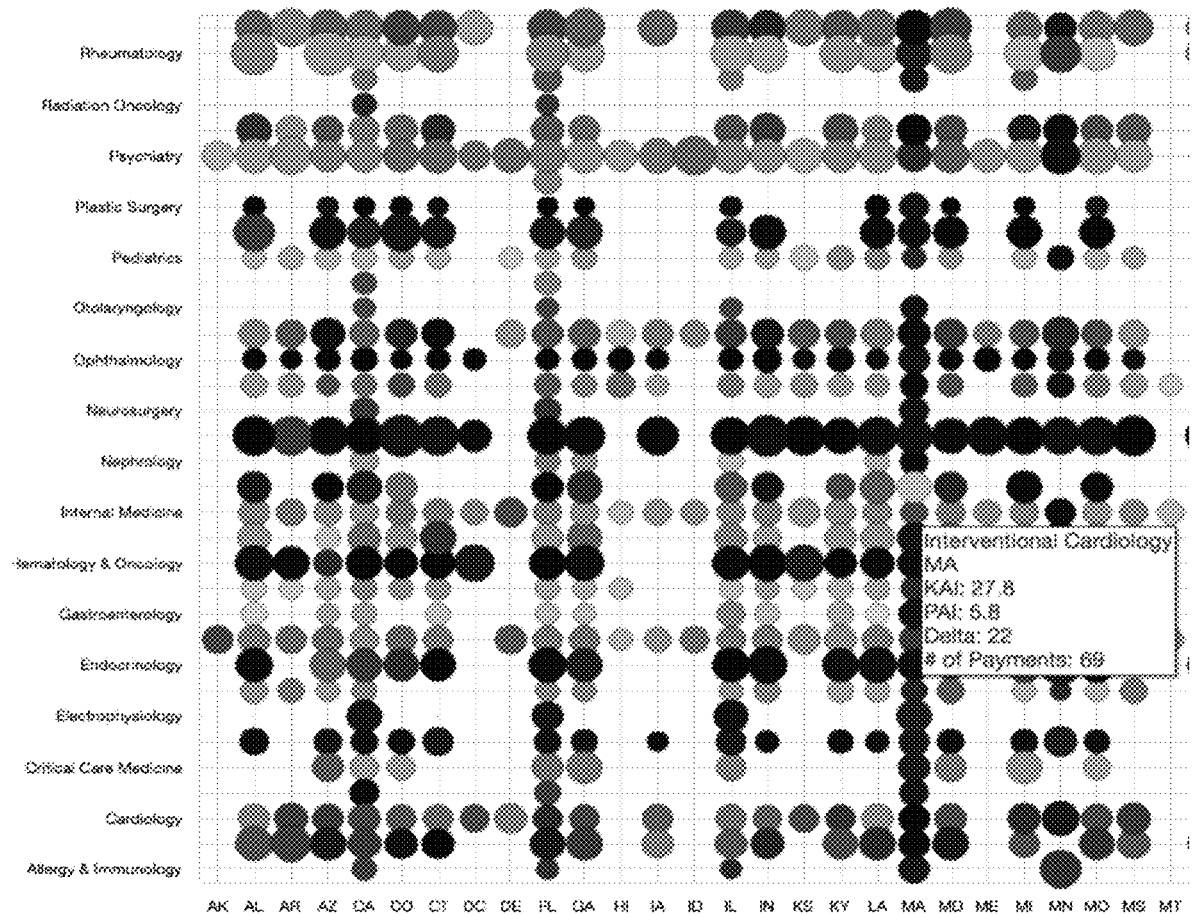
FIG. 2C is a screen shot depicting one embodiment of a description of a level of expertise for each of a plurality of profiled professionals.

Referring now to FIG. 2C, a screen shot depicts one embodiment of a description of a level of expertise for each of a plurality of profiled professionals. As shown in FIG. 2C, the analysis engine 202 may generate an index 226 of levels of expertise for each of a plurality of professionals; the index may be referred to as an affinity index. The index 226, by way of example, may include listings of specialties or types of professionals and regions in which the professionals work and include an interface with which users may compare levels of expertise of various professionals.

Figure 2D:
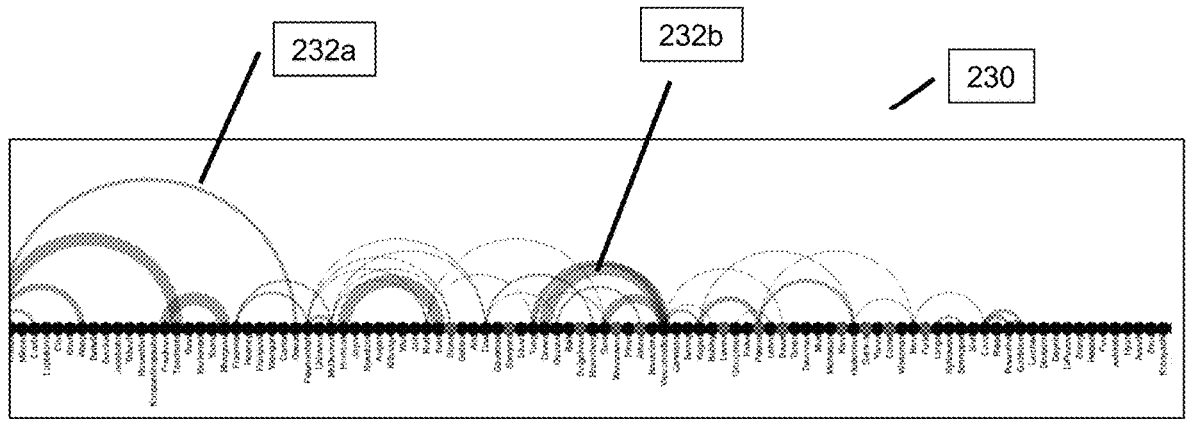
FIG. 2D is a screen shot depicting an embodiment of a description of a level of expertise for each of a plurality of profiled professionals.

Referring now to FIG. 2D, a screen shot depicts one embodiment of a description of a level of expertise for each of a plurality of profiled professionals. As shown in FIG. 2D, the analysis engine 202 may generate a graphical depiction 230 of the varying levels of expertise of a number of profiled professionals. As an example, the graphical depiction 230 may include a line 232 connecting two professionals to indicate a connection and may use a characteristic of the line 232, such as a width of the line 232, to indicate a level of expertise the professionals have on each other. By way of example, line 232a is a much thinner line than line 232b and, in one embodiment, this may indicate that the professionals connected by line 232a are not as influential on one another as the professionals connected by line 232b.

The system 200 may include a workflow engine 208. In one embodiment, the workflow engine 208 maintains a state for one or more processes managed by the first computing device 106a. For example, the workflow engine 208 may record a status of a profile being analyzed by the analysis engine 202. As another example, the workflow engine 208 may record a status indicating that the analysis engine 202 has generated a recommendation of a physician's profile to transmit to an operator in connection with a referral. In embodiments in which the machine 106a provides scheduling resources facilitating a connection between, for example, a plurality of professionals, the workflow engine 208 may record a status of the scheduling process. In embodiments in which the first computing device 106a provides functionality facilitating an authorization of a connection between a physician and a patient (e.g., by confirming that an insurance company authorizes an appointment between a physician and a patient), the workflow engine 208 may record a status of the authorization process (e.g., generate a data structure and store therein an indication of the status). In embodiments in which the machine 106a provides functionality facilitating generation and transmission of customized disclosure reports on behalf of a professional, the workflow engine 208 may record a status of a customized disclosure report as the customized disclosure report is, for example, generated, approved for transmission, and filed with the appropriate entity. In some embodiments, the workflow engine 208 provides status reports to other components executing on, or in communication with, the first computing device 106a. In other embodiments, the workflow engine 208 provides status reports to other computing devices, such as, for example, the second computing device 102 and the remote machine 106b. In some embodiments, the workflow engine 208 schedules an appointment for a professional with the subject of a referral opportunity. The workflow engine 208 may also reserve resources for an appointment that it schedules.

The second computing device 102 may be a computing device 100 as described above in reference to FIGS. 1A-1C. In some embodiments, the second computing device 102 is a computing device operated by a call center. The second computing device 102 may be operated by an operator taking calls at the call center. In some embodiments, the second computing device 102 includes a speech-to-text converter 210. In one of these embodiments, the speech-to-text converter 210 receives a stream of audio data containing audio contents from the call while the call is in progress. The stream may include audio data originating from an operator at the call center, audio data originating from the patient calling the operator, or both; for instance, the audio stream may include both questions or other prompts provided by the operator and the responses thereto by the patient.

In one embodiment, the speech-to-text converter 210 is executed by the second computing device 102. In one such embodiment, the second computing device 102 is the device executing an application with which the operator communicated with the calling patient (e.g., via softphone or videoconferencing application). In another such embodiment, a third computing device (not shown) transmits the audio data received during the call to the second computing device 102; for example, a telephone used by the operator may transmit the audio data.

In another embodiment, the speech-to-text converter 210 is executed by the first computing device 106a. In one such embodiment, the second computing device 102 may transmit the audio data received during the call to the first computing device 106a. In another such embodiment, a third computing device (not shown) transmits the audio data received during the call to the first computing device 106a; for example, a telephone used by the operator may transmit the audio data or a mobile phone operated by the patient may include speech-to-text conversion functionality.

In one embodiment, regardless of where the speech-to-text converter 210 executes, the speech-to-text converter 210 converts the audio into text and transmit the text to the analysis engine 202 for analyses. The outcome of the analyses and recommendations, referrals, or requests for additional information may be transmitted to the second computing device for display to the operator.

In one embodiment, the second computing device 102 includes a presentation engine 212 that provides an operator with access to the analytics data generated by the analysis engine 202. The presentation engine 212 may generate one or more user interfaces 214. In some embodiments, the operator may access a user interface 214 generated by the presentation engine 212 in order to generate queries; for example, the operator may view data generated by the analysis engine 202 (such as, by way of example, an enumeration of potential referrals) and make requests for identifications of physician profiles or requests for identifications of individuals who satisfy requirements for referrals, via the presentation engine 212. In some embodiments, the presentation engine 212 is provided by the first computing device 106a, for example as a web site including at least one user interface which operator may access.

The user interface 214 may display data concerning the patient to the operator; for instance, the user interface 214 may receive data extracted by the speech-to-text converter 210 and display the data to the operator by means of a display device 124a-n, as disclosed above in reference to FIGS. 1A-1C. The user interface 214 may display data concerning potential referrals and scheduling information, retrieved by the analysis engine 202 as disclosed in further detail below, using a display device 124a-n as disclosed above in reference to FIGS. 1A-1C. In some embodiments, the system automatically and dynamically modifies a display of the user interface 214 based upon the data analyzed by the analysis engine 202. In other embodiments, the data is provided to the operator by an audio device; for instance, the data may be provided to the operator via a headset (not shown).

In some embodiments, a third computing device 102b (shown in shadow in FIG. 2A) is operated by a patient using a voice interface application (e.g., SIRI or ALEXA) to interface with a service provided by a healthcare or health-related organization (e.g., a doctor's office or insurance company). The third computing device 102b may provide the patient with access (e.g., via a web browser application) to the presentation engine 212, as well as to any other software applications made available by the second computing device 102a. By way of example, the patient may interact with the voice interface application (e.g., by speaking into a microphone or other audio input device of the third computing device 102b), which generates an audio stream from the patient voice. The third computing device 102b may execute a speech-to-text converter 210 and convert the audio stream to text. Alternatively, the third computing device 102b may transmit the audio stream to another computing device (e.g., the second computing device 102b) for conversion of the speech into text. The methods and systems described herein provide functionality for using the converted text to prompt the user for additional information.

The methods and systems described herein provide functionality for using the converted text to modify another application (e.g., by modifying data displayed by the user interface 214, the presentation engine 212, or other software made available to the third computing device). The methods and systems described herein provide functionality for using the converted text to modify a search executed (and in some embodiments to generate a new search for automatic execution) based upon a request received from the third computing device 102b (e.g., via interaction with a user interface or via interaction with the voice interface application).

Figure 2E:
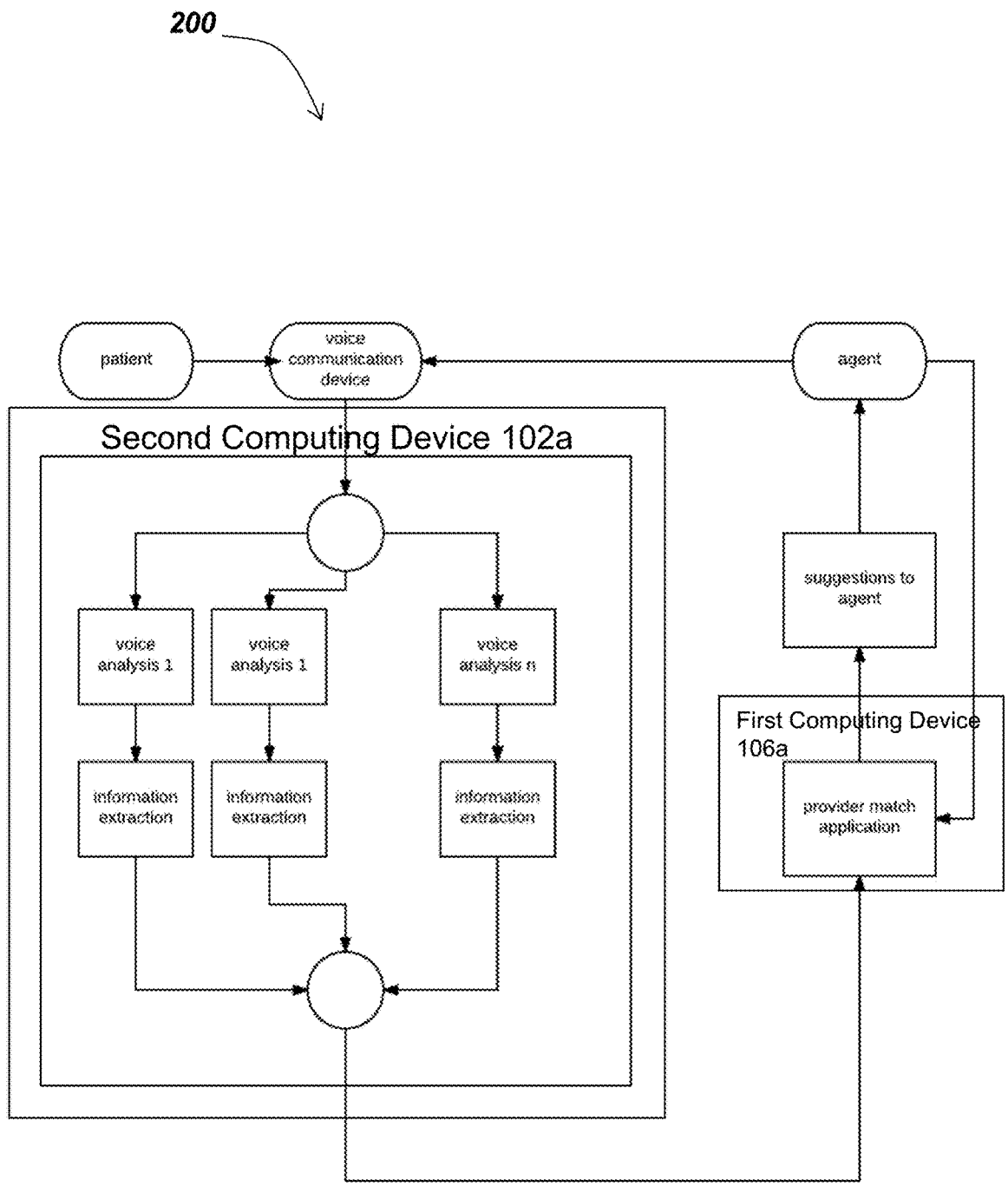
FIG. 2E is a block diagram depicting one embodiment of a system in which a user accesses a voice communication device in order to interact with an agent at a call center.

Referring now to FIG. 2E, a block diagram depicts one embodiment of a system 200 in which a user accesses a voice communication device in order to interact with an agent (e.g., a call center agent). As depicted in FIG. 2E, the user's voice communication device may transmit audio data (e.g., generated based upon the patient user's utterances) to a second computing device 102a, which performs voice analysis and information extraction; the second computing device 102a may transmit extracted information to the first computing device 106a (e.g., to a referral application) for use in generating suggestions to the agent for interacting with the patient user. The second computing device 102a may be associated with the user (e.g., a phone or computer of the user). The second computing device 102a may be associated with the call center (e.g., a phone or computer of the call center). The second computing device 102a may be associated with a third party. In alternate embodiments, the first computing device 106a provides the functionality of the second computing device 102a.

Figure 2F:
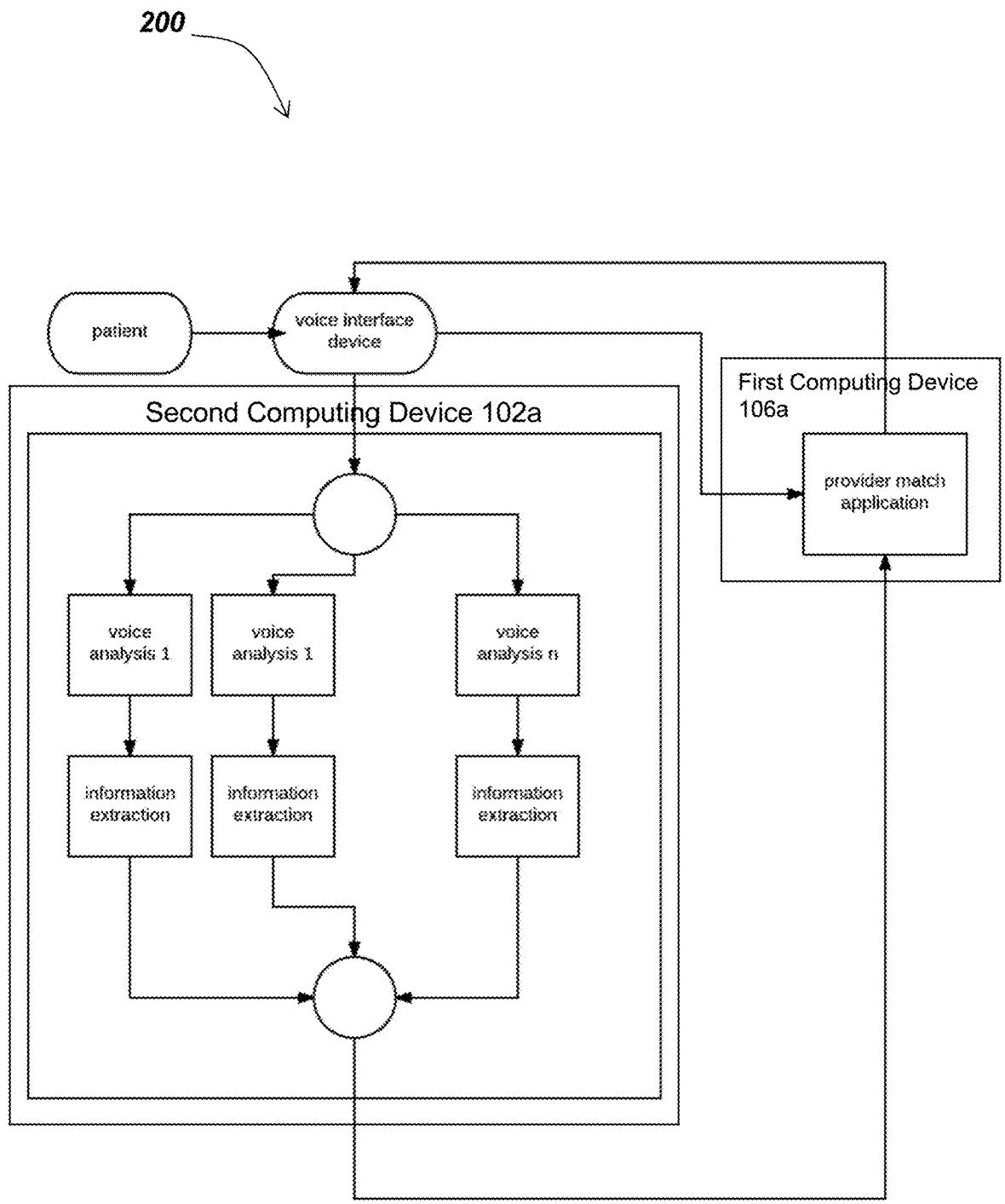
FIG. 2F is a block diagram depicting one embodiment of a system in which a user accesses a voice communication device in order to interact with a hosted application executed by a computing device at a location remote from the voice communication device.

Referring now to FIG. 2F, a block diagram depicts one embodiment of a system in which a user accesses a voice communication device in order to interact with a hosted application executed by a computing device at a location remote from the voice communication device. As depicted in FIG. 2E, the user's voice communication device may transmit audio data (e.g., generated based upon the patient user's utterances) to a second computing device 102a, which performs voice analysis and information extraction; the second computing device 102a may transmit extracted information to the first computing device 106a (e.g., to a referral application) for use in generating responses, recommendations, modified displays, and other interactions with the user.

Referring back to FIG. 2A, in some embodiments, the first computing device 106a integrates with one or more remote machines 106 to provide the functionality described herein.

For example, in one embodiment, the first computing device 106a is in communication with a remote machine 106b that provides access to one or more electronic medical records. The first computing device 106a may use the electronic medical records to identify data associated with the profiled physician (e.g., outcomes of patients previously treated by a physician) and data associated with the patient (e.g., a case history, diagnoses, previous effective treatments, or other patient data). As another example, the first computing device 106a may be in communication with customized databases (e.g., databases containing patient or physician data). As a further example, the first computing device 106a may be in communication with scheduling systems, eligibility lookup systems, and clinical environments generally.

In some embodiments, the first computing device 106a is in communication with a bidding system (not shown). For example, the first computing device 106a may incorporate or be in communication with a financial market bidding system in which healthcare providers bid for referral opportunities based on at least one of price and quality (e.g., allowing a referring physician to identify the best doctor available for the lowest fees). An entity such as an accountable care organization may make a determination as to what tests or procedures they are willing to offer at particular price points in order to qualify for particular referral opportunities.

The profile generator 204, analysis engine 202, workflow engine 208 and presentation engine 212 may operate on one or more computing devices in various combinations. For instance, in some embodiments, the profile generator 204, analysis engine 202 and presentation engine 212 operate on a first computing device 106a and the workflow engine 208 executes on a third computing device (not shown); in other embodiments, the third computing device is the same device as the first computing device 106a, such that the workflow engine 208 executes on the same device as the profile generator 204, analysis engine 202, and presentation engine 212. Skilled practitioners in the art will be aware of many other possible combinations of remote devices on which one or more of the profile generator 204, analysis engine 202, workflow engine 208, or presentation engine 212 may operate.

Figure 3A:
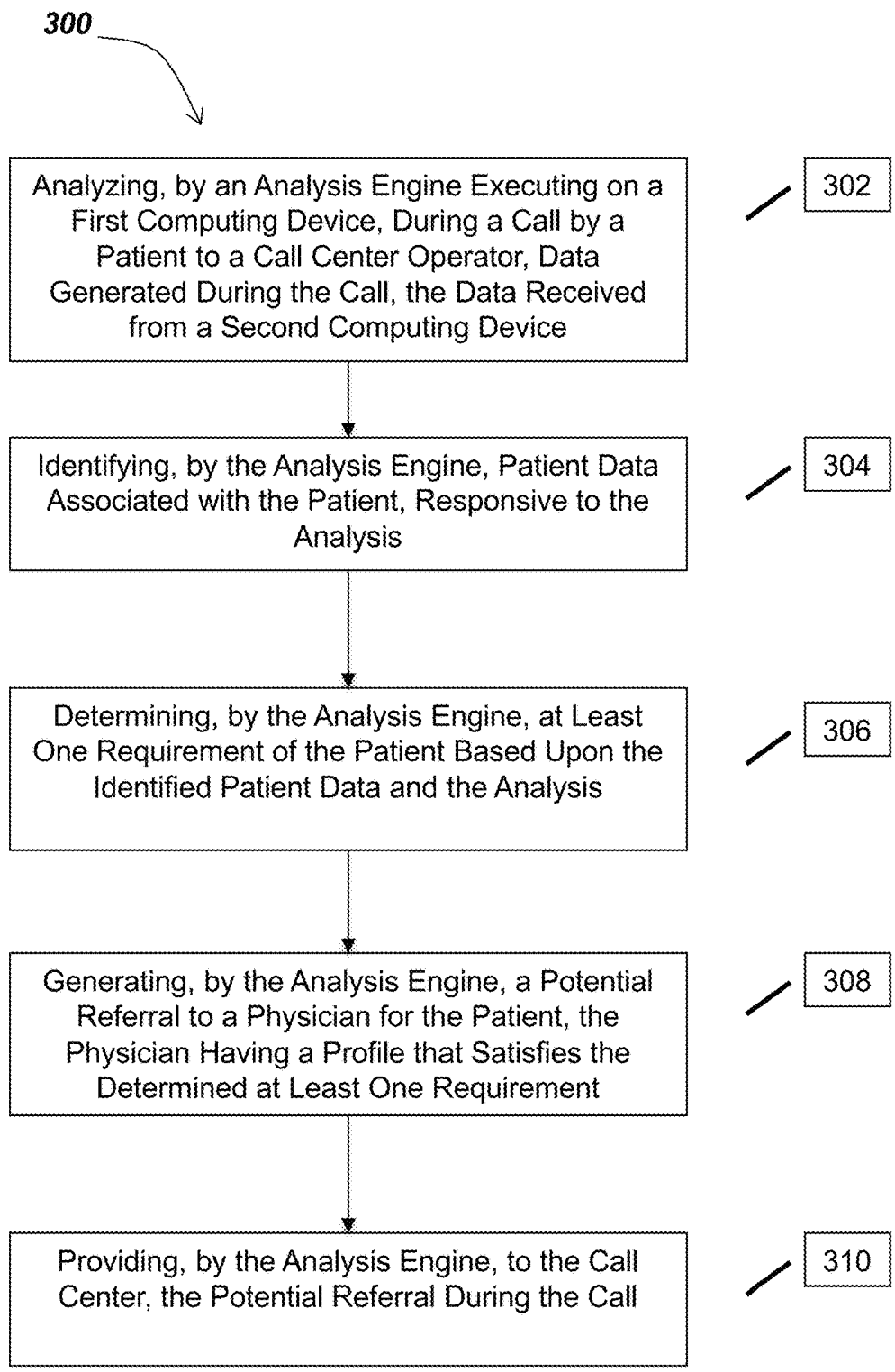
FIG. 3A is a flow diagram depicting an embodiment of a method for analyzing speech to generate a potential referral.

Referring now to FIG. 3A, a flow diagram depicts one embodiment of a method 300 for analyzing speech to generate a potential referral. In brief overview, the method 300 includes analyzing, by an analysis engine executing on a first computing device, during a call by a patient to a call center operator, data generated during the call, the data received from a second computing device (302). The method 300 includes identifying, by the analysis engine, patient data associated with the patient, responsive to the analysis (304). The method 300 includes determining, by the analysis engine, at least one requirement of the patient based upon the identified patient data and the analysis (306). The method 300 includes generating, by the analysis engine, a potential referral to a physician for the patient, the physician having a profile that satisfies the determined at least one requirement (308). The method 300 includes providing, by the analysis engine, to the call center, the potential referral during the call (310). In one embodiment, providing the potential referral during the call includes modifying, by the analysis engine, a user interface displayed to the call center, during the call, the modification to the display including addition of an identification of the potential referral.

Referring now to FIG. 3A in greater detail, and in connection with FIGS. 2A-2E, the method 300 includes analyzing, by an analysis engine executing on a first computing device, data generated during a call by a patient to a call center, the data received from a second computing device (302). In some embodiments, the analysis engine 202 receives the data from a speech-to-text converter 210; for example, the data may be created by a speech-to-text converter 210 executing on the second computing device 102, based on an audio data stream generated during an operator-patient call. The speech-to-text converter 210 may execute on any machine 100 at a call center, including an operator's computing device 102 or phone or a third computing device 100 (not shown) dedicated to executing the speech-to-text converter 210. In alternative embodiments, the analysis engine 202 receives the audio stream and executes the speech-to-text converter 210 to generate the data. As indicated above, the call may be a telephone call directly to a call center or may be an interaction with a voice-operated interface (e.g., SIRI or ALEXA) in which the converted text is transmitted to the call center or to a human agent for further assistance. Alternatively, in some embodiments, there is no interaction with a call center, as a user may interact exclusively with an application provided over a network connection and user utterances to a voice-operated interface may be converted into text and sent to the application without routing through a call center or to a human agent.

The received data may include text data produced via a textual chatting conversation, such as a simple message service (SMS) chat, or a chat performed via an instant messaging protocol, which may also include audio data transmitted using the chat or instant messaging protocol. In some embodiments, the original audio data is also transmitted to the analysis engine 202.

The received data may include information identifying the patient. The information may include the patient's name. The information may include the patient's date of birth. The information may include the patient's social security number. In some embodiments, the data includes medical history data from the patient; for instance, the operator may ask the patient to describe personal or family history of medical conditions. The data may include allergies the patient has to medication. The data may include descriptions of past procedures performed on the patient. In other embodiments, the data includes personal preferences of the patient; for instance, the operator may request that the patient specify a preferred distance from the patient's residence for a visit to take place. The data may specify whether the patient prefers a male or female physician. In some embodiments, the patient is provided, by the operator, with a list of profiled physicians, and is provided with an opportunity to select a preferred physician. The list may include photographs of the listed physicians transmitted to the patient via a communications session separate from the call. The list may include biographical information concerning the listed physicians. The list may include practice areas of the listed physicians.

The data may include the patient's current needs; for instance, the patient may be prompted to describe the category of visit the patient is seeking. The patient may be prompted to describe a symptom from which the patient is suffering. The patient may be prompted to describe a condition with which the patient has been diagnosed. The patient may be prompted to describe a medication the patient is currently taking. The patient may be prompted to describe a treatment the patient is currently receiving.

In some embodiments, the data includes data pertaining to the phone call itself. The data may include the phone number from which the patient is calling. The data may include the time at which the call occurs. The data may include the date on which the call occurs. The data may include the geographical location from which the patient is calling; the geographical location may be provided by a device operated by the patient, such as a mobile device that can self-locate using the global positioning system (GPS) or similar technology. The geographical location may be determined using textual data entered by the patient, for instance in response to an automated phone system prompt asking for the patient's geographical location. The data may include audio data.

In some embodiments, the analysis engine 202 analyzes the data to identify at least one key word in the data. Examples of key words may include words relating to symptoms (e.g., "rash") or to medical procedures (e.g., "surgery") or specific conditions (e.g., "diabetic").

In some embodiments, a variety of types of information are extracted from the data and analyzed by the analysis engine 202. In some embodiments, the analysis engine 202 executes an information extraction engine (not shown) for extracting information from converted text. In one embodiment, speech content is extracted. The system 200 may extract information from patient voice by transcribing the voice into text and extracting the information using natural language processing (NLP) techniques such as tokenization, tagging, entity recognition and information extraction. The system 200 may classify the extracted information into parameters such as clinical need, location, timing/urgency, etc. so that the information can be meaningfully applied to improve search. In a call center scenario, such analysis can help the agent streamline the conversation and provider faster and better quality service to the patient. For example, if patient asks to see a doctor for recurring cough, the system identify that the symptom has been identified and prompt the agent that other information is needed, e.g. severity, in order to provide a better match. Recognizing this information directly from the speech, enables surfacing the questions the agent needs to ask without the agent needing to type the information into the application. Additionally, decoding the content of patient's speech can help the agent help with terms (conditions or symptoms) that he/she may be unfamiliar with.

In another embodiment, the analysis engine 202 analyzes the data and identifies sentiment data. The system 200 may analyze the patient voice to determine sentiment (negative, positive) of the speaker. The sentiment data may include an identification of sentiment expressed by the patient during the call. The sentiment analysis can be used as a feedback mechanism providing feedback to the call center operator (also referred to herein as an agent) identifying the patient sentiment during the conversation with the patient. The system may modify a user interface generated and displayed to the call center operator during the call to identify the patient sentiment, in order to provide feedback to the operator while the operator is still speaking to the patient. For instance, a positive trend in sentiment can be used as feedback to the agent that they are meeting patient's expectations in providing them the service. Similarly, the analysis can be used in a scenario where the patient is using the voice interface. This information can be later used to evaluate quality of service (by the access center, or directly via voice interface) to make improvements.

In still another embodiment, the analysis engine 202 analyzes the data and identifies an emotional state of the speaker. The analysis engine 202 may analyze a patient's voice to determine a patient's emotion that can be relevant for processing request (or, more particularly, the analysis engine 202 may analyze a digital representation of a patient's voice to identify characteristics of the digital representation that are correlated with one or more emotions). Emotions such as anger, joy, fear, sadness, and surprise can be inferred from one's speech by analyzing not only the speech content (linguistic features, e.g. words used), but also the acoustic features such as pitch, intensity, duration, and more complex features such as voice quality, spectrum, etc. At least one acoustic feature may be identified in the data generated from the patient's voice during the call. Emotional information from the patient's voice can be used to extract additional relevant information. For example, the analysis engine 202 can generate an inference that indicated emotional profile indicates urgency of the need, or severity of the condition. This information can then be used to guide the agent in the access center to add additional criteria (e.g. searching for severe headache vs. headache, or available same or next day) to find a more appropriate provider. The system may modify a user interface displayed to the call center operator during the call to include feedback regarding the patient emotion. Similarly, in the voice interface scenario, the system may respond with asking the patient if they needed a next day appointment, or even direct the patient to emergency care. In some embodiments, the determined sentiment data may also be used to extract additional relevant information.

In still another embodiment, the analysis engine 202 analyzes the data and identifies one or more personality traits of the speaker. The analysis engine 202 may analyze the conversation to inform patient's personality traits that can be used to assist matching patient to the best provider. Personality may be important when matching patents to providers, especially when patients are looking for primary care physician or a pediatrician. The analysis engine 202 may use patient's speech collected during the conversation and process it via personality analysis service (such as IBM WATSON's personality Insights). The profile can be expressed using the dimensions such as agreeableness, conscientiousness, extraversion, emotional range, and openness. The profile can, then be matched to provider's profile that is most complementary to the patient's (e.g., by identifying a characteristic of a provider profile, such as a physician profile, the characteristic indicating the provider has a personality trait complementary to the identified at least one personality trait of the patient). The analysis engine 202 may keep the history of conversations with the patient to refine and adjust the profile over time by including the conversations in the updated analysis. This analysis is applicable in both call center and voice interface scenario.

While each type of extracted information (including, without limitation, content, emotion, sentiment and personality data as described above) can be leveraged individually to extract and/or infer additional information from patient's voice, the analysis engine 202 may also use a combination of these elements to determine what the optimal response might be. This can be done using (a subset of) extracted elements as features and training a model using a machine learning algorithm.

The analysis engine identifies patient data associated with the patient, responsive to the analysis (304). In some embodiments, the analysis engine 202 identifies patient data within a record accessible to the call center (e.g., a patient record). In other embodiments, the analysis engine 202 identifies an electronic medical record associated with the patient. In further embodiments, the analysis engine 202 uses a keyword identified during an analysis of the received data to identify patient data of any type. For instance, the analysis engine 202 may extract one or more key words relating to, without limitation, a patient name, social security number medical history, recent procedural history, or other type of data that would be stored in, for example, an electronic medical record.

In one embodiment, the analysis engine 202 retrieves electronic medical records associated with the patient; for example, by using patient-identifying data identified in the data received from the second computing device 102. In some embodiments, the analysis engine 202 retrieves the electronic medical records from a remote machine 106b; for instance, the analysis engine 202 may retrieve the electronic medical records from a server operated by a hospital. The analysis engine 202 may retrieve the electronic medical records from a database containing electronic medical records. The analysis engine 202 may retrieve the electronic medical records from a cloud service maintaining electronic medical records. The analysis engine 202 may analyze data within the electronic medical record to provide feedback to the call center operator during his call with the patient.

In some embodiments, the analysis engine 202 uses data obtained during the call to inform the process of further data extraction during the call; for example, to prompt the operator to ask additional questions. As another example, where the analysis engine 202 has identified some data associated with the patient, the analysis engine 202 may use that data to aid in resolving ambiguous speech-to-text results; as an example, if the analysis engine 202 has retrieved electronic medical records of the patient, the analysis engine 202 may resolve ambiguous speech-to-text results in favor of medical conditions or needs consistent with the medical history provided in the electronic medical records. In some embodiments, the analysis engine 202 provides ambiguity-resolving information to the speech-to-text converter 210 to aid in future speech-to-text conversion (e.g., conversion of audio data generated later in the call). In other embodiments, the analysis engine 202 uses the partial data to present lists of potential related vocabulary to a user, such as the operator. For instance, the presentation engine 212 may display data received from the second computing device 102 and data retrieved from the analysis engine 202 during the call; in some embodiments, the presentation engine 212 may further provide vocabulary related to the provided data to aid the operator in further discussion with the patient. As an example, the further vocabulary may be presented to the operator in the form of lists of options to enter in a form field. The presentation of the suggested terms may be specific to a particular operator.

The analysis engine determines at least one requirement of the patient based upon the identified patient data and the analysis (306). In one embodiment, the analysis engine 202 may match a key word extracted from the received data with a term in a taxonomy system accessible to the first computing device 106a in order to determine the at least one requirement.

The at least one requirement may include a medical service the patient requires; for instance, the patient may need a particular form of surgery. The patient may need a particular diagnostic procedure, such as an Mill to determine the cause of joint pain, or a blood test for one or more medical conditions. As another example, the patient may be calling to schedule an appointment with a specialist as recommended during an appointment with the patient's primary care physician.

In other embodiments, the at least one requirement is a symptom to be investigated. For instance, the patient may tell the operator that a part of the patient's body is hurting. The patient may have sustained an injury requiring medical examination. The patient may have suffered from a fainting spell. The patient may describe other symptoms such as chest pain, numbness, affected vision or hearing, or digestive problems.

In some embodiments, the analysis engine 202 uses patient data to determine likely at least one requirement. For instance, if the patient information indicates a recently performed orthopedic surgery, the analysis engine 202 may list medical procedures that are likely to follow such a procedure; for instance, the operator may be presented with list items corresponding to suture removal, physical therapy, complications such as potential infection, and other possible issues, which may allow the operator to ask the patient specific questions about the patient's current needs. The analysis engine 202 may retrieve a collection of terms related to a current condition of the patient, and determine at least one requirement using the collection of terms. For instance, if retrieved electronic medical records indicate that the patient is diabetic, and the patient describes an eye or leg complaint, the analysis engine 202 may have a set of terms related to diabetic conditions to which the patient's provided information may be compared. In some embodiments, the analysis engine 202 repeatedly compares data received during the call to data stored in the system 200 to add, refine, or modify requirements.

In some embodiments, the analysis engine 202 matches a term from the data to a search term within a taxonomy system operated on the first computing device 106a, and generates an alert based on the matched term.

In some embodiments, the analysis engine 202 receives instructions from the operator concerning the patient's at least one requirement. In some embodiments, the operator asks the patient questions to clarify the patient's statements, and modifies the data using the user interface 214 based on the patient's responses.

In another embodiment, in which a patient has contacted an organization associated with a plurality of physicians and requested assistance with a condition, the operator may determine that the first individual should be referred to a primary care physician, specialist, or other healthcare professional and generate a request for identification of an appropriate physician with which to connect the patient. For example, a patient may contact a hospital (e.g., via telephone or electronic communications) and request access to a doctor to treat a condition; an operator interacting with the patient may transmit a request to the analysis engine 202 for an identification of a physician able to see the patient in connection with the condition. In another embodiment, the analysis engine 202 makes an identification of a profiled physician qualified to accept the potential referral based upon the received information (e.g., the identification of the potential referral, an identification of a diagnoses, and at least one requirement of the potential referral) and an analysis of one or more physician profiles.

The at least one requirement may include further needs or preferences of the patient. For instance, the at least one requirement may include a geographical preference, such as a distance from the patient's residence within which the patient would prefer to have the appointment. The at least one requirement may include a preference regarding the physician to perform the appointment, such as a preference that the physician be male or female. In other embodiments, the at least one requirement includes a clinical effectiveness requirement, as described in further detail below. The at least one requirement may include an operational at least one requirement, as described in further detail below. The at least one requirement may include a financial at least one requirement, as described in further detail below. The at least one requirement may include a verification at least one requirement, as described in further detail below.

The analysis engine generates a potential referral to a physician for the patient, the physician having a profile that satisfies the determined at least one requirement (308). In some embodiments, the analysis engine 202 generates the potential referral by determining that a profile satisfies the at least one requirement. In one embodiment, the analysis engine 202 analyzes a characteristic of the profile to determine whether the generated profile satisfies the at least one requirement. In some embodiments, the analysis engine 202 accesses the affinity index described above in connection with FIG. 2C in determining that the generated profile satisfies the at least one requirement. In other embodiments, the analysis engine 202 applies weights to one or more professional connections of the profiled physician based on the relevance of attributes to the requirements (so that, for example, relevance changes based on the nature of the requirements). In further embodiments, the analysis engine 202 may access claims data in making the determination.

Figure 3B:
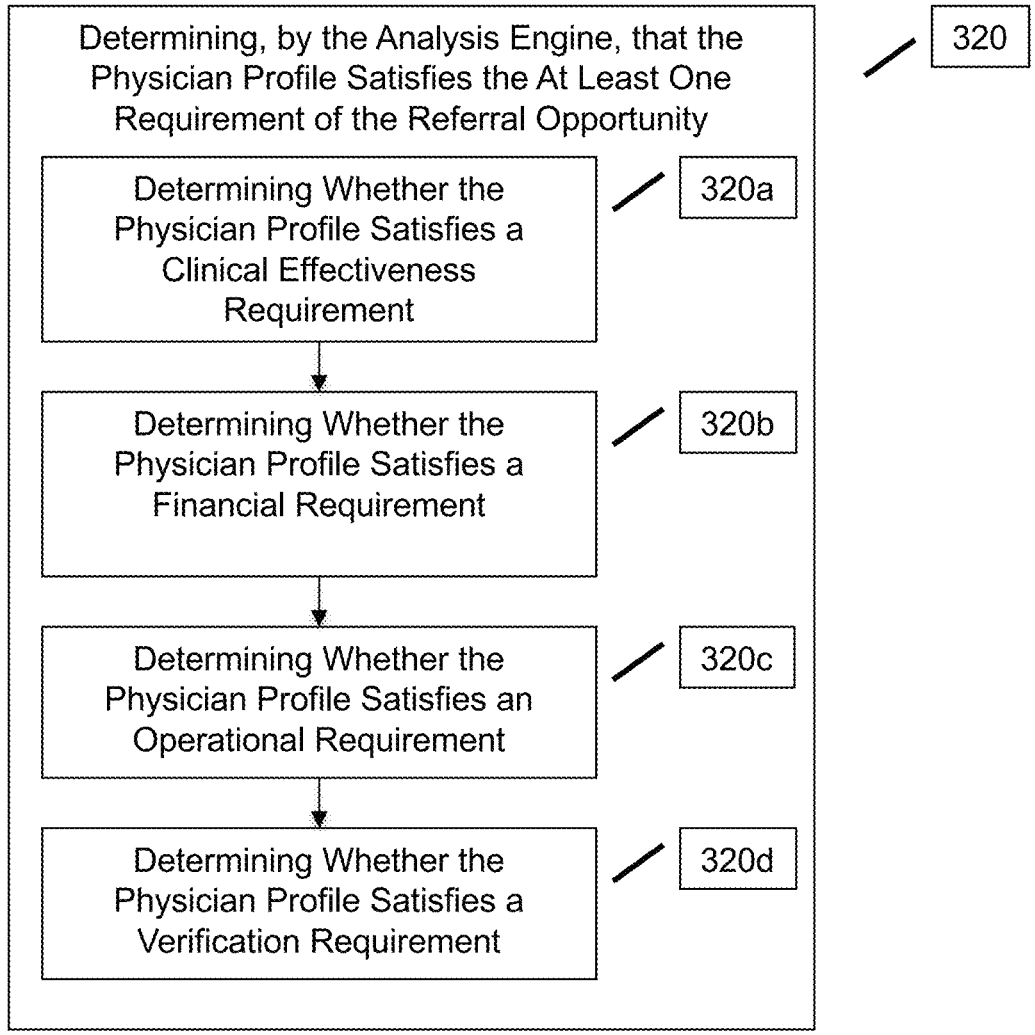
FIG. 3B is a flow diagram depicting an embodiment of a method for matching a professional with a referral opportunity.

Referring ahead to FIG. 3B, a flow diagram depicts an embodiment of the method described in connection with FIG. 3A. As shown in FIG. 3B, the method includes determining, by the analysis engine, that the physician profile satisfies the at least one requirement of the referral opportunity (320); the determination may include several sub-determinations before the analysis engine 202 concludes, based on the analyses, that a particular physician is qualified for a particular potential referral. As depicted in FIG. 3B, determining that the physician profile satisfies the at least one requirement may include determining whether the physician profile satisfies a clinical effectiveness requirement (320a). Determining that the physician profile satisfies the at least one requirement may include determining whether the physician profile satisfies a financial requirement (320b). Determining that the physician profile satisfies the at least one requirement may include determining whether the physician profile satisfies an operational requirement (320c). Determining that the physician profile satisfies the at least one requirement may include determining whether the physician profile satisfies a verification requirement (320d). Alternative embodiments of determining that the physician profile satisfies the at least one requirement (306) may include making a sub-set (e.g., some, all or none) of the determinations described in connection with FIG. 3B; in other words, the analysis engine 202 may determine that the physician profile satisfies each of a plurality of requirements. As an example, the analysis engine 202 may select the physician profile only if the analysis engine 202 determines that the physician profile satisfies both a clinical effectiveness requirement and a financial requirement. The assessment of multiple requirements may enhance the effectiveness of the matching algorithm by taking advantage of the multifaceted profile data produced as described above in reference to FIG. 3A.

Determining that the physician profile satisfies the at least one requirement may include determining whether the physician profile satisfies a clinical effectiveness requirement (320a). In one embodiment, determining whether the physician profile satisfies a clinical effectiveness requirement may include, for example and without limitation, determining whether the profiled physician satisfies a requirement regarding a particular clinical experience or a requirement regarding a level of quality of care provided by the profiled physician. In another embodiment, the analysis engine 202 determines that the profiled professional or entity is associated with an area of specialty identified in the at least one requirement. For example, the analysis engine 202 may determine whether the profiled physician or entity is associated with an area of specialty identified in the at least one requirement. As another example, the requirement may specify, without limitation, a case history of the profiled physician, a number of referrals to the profiled physician by other industry professionals, or prior patient outcome (e.g., statistical data on patient outcomes for patients seen by the profiled physician, such as rate of readmission or patient compliance with medical treatment).

In some embodiments, the analysis engine 202 determines whether the physician profile satisfies a clinical effectiveness requirement by determining that the profiled physician has a sufficient workload in an area of specialty identified in the at least one requirement. For instance, research regarding medical fields indicates that a minimum threshold of clinical fluency is critical in providing appropriate patient care; thus, in one embodiment, the analysis engine 202 may determine that the profiled physician is more likely to meet the clinical effectiveness requirement if the profiled physician performs more than a certain threshold number of procedures similar to a procedure specified in the referral opportunity. Professionals in other fields also may require workload exceeding a certain threshold to achieve maximal effectiveness.

Figure 3C:
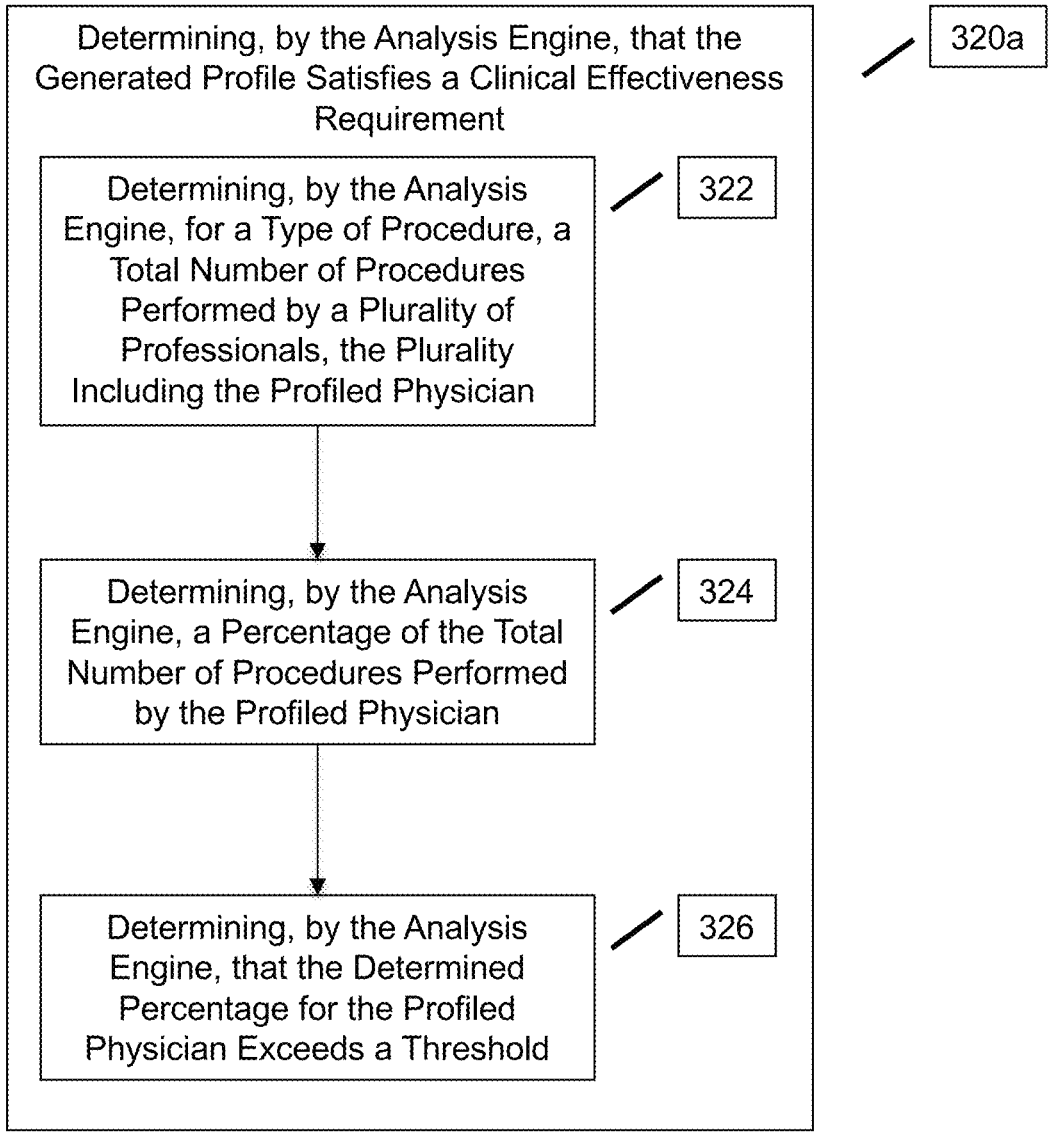
FIG. 3C is a flow diagram depicting an embodiment of a method for determining clinical effectiveness based on workload.

FIG. 3C illustrates steps for determining that the professional has sufficient workload in an area of specialty in some embodiments. In one embodiment, determining that the physician profile satisfies a clinical effectiveness requirement (320a) involves determining, by the analysis engine 202, for a type of procedure, a total number of procedures performed by a plurality of physicians, the plurality including the profiled physician (322); determining, by the analysis engine, a percentage of the total number of procedures performed by the profiled physician (324); and determining, by the analysis engine, that the determined percentage for the profiled physician exceeds a threshold (326).

Referring to FIG. 3C in more detail, and by reference to FIGS. 2A-3B, the analysis engine 202 may determine, for a type of procedure, a total number of procedures performed by a plurality of professionals, the plurality including the profiled physician (322). The plurality of professionals may be some or all of the professionals that work for the entity for which the profiled professional works. For instance, the plurality of professionals may be the set of professionals that work in a particular department with the profiled physician. In one embodiment, the plurality of professionals is a plurality of physicians employed by an organization such as a hospital. In another embodiment, the plurality of professionals is a plurality of physicians that work in a particular medical field within the hospital, such as a cardiology department at the hospital. Although the methods and systems described herein provide functionality applicable to organizations with any number of physicians, such methods and systems may be particularly helpful in managing organizations with large numbers of physicians. For example, some hospitals (or networks of affiliated hospitals) may employ hundreds or even thousands of physicians and implementing functionality for optimizing patient allocation may be particularly beneficial to such organizations. The plurality of professionals may be some or all of the professionals that work in a geographic region in which the profiled professional works. The plurality of professionals may be some or all of the professionals belonging to a professional organization in which the profiled physician is a member.

In some embodiments, an entity employing the profiled physician provides the data analyzed by the analysis engine 202. For instance, the healthcare organization employing the physician may provide the data analyzed by the analysis engine 202. In one embodiment, the analysis engine 202 accesses a scheduling database to determine the total number of procedures performed by the plurality of professionals. In another embodiment, the analysis engine 202 accesses an electronic medical record database to determine the total number of procedures performed by the plurality of professionals. In still another embodiment, the analysis engine 202 accesses a billing database to determine the total number of procedures performed by the plurality of professionals. In yet another embodiment, the analysis engine 202 accesses a claims database (e.g., a database of claims made to insurance companies for reimbursement) to determine the total number of procedures performed by the plurality of professionals. The data collected for this analysis may be incorporated in a profile as described above in reference to FIGS. 2B-2C; the data may be regularly updated along with other data in the profile, for instance by repeatedly querying databases, remote devices, or institutions possessing the data. The data may also be updated in response to events detected by the analysis engine 202; for instance, if the profiled physician changes employers, the analysis engine 202 may, upon receiving data describing the change of employment, collect data concerning a new plurality of professionals representing the new colleagues of the profiled physician.

In some embodiments, the analysis engine 202 accesses at least one database of procedure-related data, the at least one database undergoing modification by one or more entities. For example, a hospital may authorize the analysis engine 202 to access "live" databases such as scheduling databases that are actively used to create and modify scheduling data related to the type of procedure. Providing the analysis engine 202 with access to databases that are in use and subject to ongoing modification may allow the analysis engine 202 to make more accurate determinations than if the analysis engine 202 were restricted to historical data. In some embodiments, the analysis engine 202 receives access to both databases of historical data and to databases subject to ongoing modification.

In one embodiment, the analysis engine 202 accesses a database 206 to determine the total number of procedures of a particular type performed by the plurality of professionals. In another embodiment, the analysis engine 202 determines the total number of procedures of the type performed during a retrospective time period (e.g., the previous day, month, quarter, year, and so on). For example, the analysis engine 202 may retrieve data from the database 206 to determine how many heart surgeries all of the physicians at a particular hospital performed during the previous year. In another embodiment, the analysis engine 202 determines the total number of procedures of the type for which the plurality of professionals have contemporaneous responsibility (e.g., on-going cases or cases assigned to the professionals as of the date of the analysis). In still another embodiment, the analysis engine 202 determines the total number of procedures of the type for which the plurality of professionals will, prospectively, have responsibility (e.g., a number of cases assigned to the professionals as of the date of the analysis plus a prediction as to how many cases the professionals will have in a future time period). A user of the system 200 may specify the time period, the type of procedure, or other data used by the analysis engine 202 during execution of the optimization method.

Determining that the profile satisfies a clinical effectiveness requirement (320a) may include determining, by the analysis engine, a percentage of the total number of procedures performed by the profiled physician (324). In one embodiment, the analysis engine 202 determines the percentage of the total number of procedures performed by each professional. For example, the analysis engine 202 may determine that 200 heart surgeries were performed in the previous year and the analysis engine 202 may determine that Doctor Smith performed 25% of those 200 heart surgeries.

The analysis engine 202 may access data stored in the database 206 to make the determination. Data may include, without limitation, information associated with an organization (such as a hospital), information associated with a professional, diagnosis code(s), procedure code(s), cost of procedure, patient length of stay in the organization, a type of admittance to the organization (e.g., emergency or elective), and a financial class of a patient (e.g., self-pay or Medicare).

As shown in FIG. 3D, the analysis engine 202 may generate a table 330 or other data structure storing the determined total number and the determined physician percentages. In one embodiment, the analysis engine 202 makes the table 330 available to users of the system 200. By way of example, and as shown in FIG. 3D, the analysis engine 202 may determine that a plurality of physicians perform 200 heart surgeries a year and store that information in table 330. Continuing with this example, the analysis engine 202 may determine that one of the plurality of physicians ("Smith" in the embodiment depicted in FIG. 3D) performed 41% of the 200 total heart surgeries while determining that a second of the plurality of physicians ("Miller" in the embodiment depicted in FIG. 3D) performed 5% of the 200 total heart surgeries.

Referring again to FIG. 3C, determining that the profile satisfies a clinical effectiveness requirement 320a may include determining, by the analysis engine, that the determined percentage for the profiled physician exceeds a threshold (326). In some embodiments, a user specifies the threshold. In other embodiments, the analysis engine 202 specifies the threshold. In some embodiments, the threshold is a percentage of a number of procedures performed by a second physician. In one of these embodiments, by way of example, the threshold is 60% of the procedures performed by the most experienced professional in the plurality of professionals. For example, and referring again to FIG. 3D, Dr. Smith may be considered the most experienced physician for heart surgeries since she has performed a greater percentage of the 200 heart surgeries performed by the plurality of physicians than any of the other physicians. The threshold in such an example would therefore be 25% (e.g., 200*0.41 is 82 heart surgeries by Dr. Smith, 82*0.6=49 heart surgeries; 49/200=25%). In such an example, Dr. Jones would exceed the threshold since he has performed more than 25% of the total number of heart surgeries, but Drs. Williams and Miller would not meet the threshold.

As indicated above, in some embodiments, the threshold is specified as a relative value (for example, without limitation, a percentage of a number of another physician's procedures). In other embodiments, however, the threshold is a range of numbers. In still other embodiments, the threshold is a specific number. For example, either a user of the system 200 or an administrator of the analysis engine 202 may specify the number, or the analysis engine 202 may be configured to use a particular number during an initialization or configuration process.

In some embodiments, the threshold is a minimum clinical fluency threshold. In one of these embodiments, the threshold is determined based on scientific research focused on a particular type of procedure. In another of these embodiments, the threshold identifies a number of procedures below which it may be unsafe to have the physician perform the procedure. By way of example and without limitation, the user or the analysis engine 202 may access data (e.g., scientific research) to determine that when a physician performs less than 5% of the total number of procedures of a particular procedure type within a time period (e.g., a year), the quality of the physician's work suffers. Work quality may be determined by a user or by the analysis engine 202 and may be determined based on scientific research. For example, work quality may be determined based on how long a physician takes to complete a procedure, how well the patient recovers from the procedure, or how much the procedure costs. As another example, the analysis engine 202 may analyze medical data associated with procedures previously performed (e.g., billing data and insurance data) and determine that when physicians perform less than 5% of a total number of heart surgeries, each surgery costs more, the physicians take more time to complete the surgery, or the patient has an increased risk of dying; in some embodiments, the determination is normalized for factors such as patient conditions (e.g., to account for the fact that some doctors may have lower success rates because they take on more complex cases). In one embodiment, and as depicted in FIG. 3D, the analysis engine 202 may store an indication of whether the determined percentage for the profiled professional exceeds the threshold. The analysis engine 202 may also rank professionals according to the degree to which they exceed the threshold, and may preferably select a physician having a higher ranking over one that exceeds the threshold to a lesser extent.

In some embodiments, analysis engine 202 may determine that the profiled physician is a good choice for the potential referral because a more experienced physician has too great a workload to perform adequately if given the referral. As another example, the analysis engine 202 may determine that, based on relative experience, although a first physician would be ideal, a second physician with less experience than the first has relatively more experience than another alternative. For example, referring to FIG. 3D, although the analysis engine 202 may identify Dr. Smith as having an optimal workload, if Dr. Smith cannot take on any additional procedures, patients, or other tasks, the analysis engine 202 may determine that a better referral candidate for the referral opportunity is Dr. Jones, who has also exceeded the threshold, although not by as much as Dr. Smith.

The system 200 may further execute a method to recalculate the workload analysis for clinical effectiveness. Therefore, in one embodiment, the methods described herein include determining, by the analysis engine, that data relating to the total number of procedures has changed, and automatically re-determining, by the analysis engine, whether the determined percentage for the profiled physician exceeds the threshold. In some embodiments, the analysis engine 202 periodically updates the threshold calculation for the profiled physician; the updating process may occur as part of the updating process for the profile. Due to the functionality provided by the system 200 for continuously re-evaluating types of procedures in a plurality of professionals, the system 200 may be said to operate automatically and in real-time.

In some embodiments, the analysis engine 202 analyzes third-party input to determine whether the physician profile satisfies the at least one requirement. For example, the analysis engine 202 may analyze data generated during the call. In another example, the analysis engine 202 may analyze data generated by a peer of the profiled physician. In a further example, the analysis engine 202 analyzes data associated with the patient; for instance, the analysis engine 202 may analyze data associated with the patient including diagnoses, past history, prior successful or unsuccessful treatments, and patient preferences.

Referring again to FIG. 3B, determining that the physician profile satisfies the at least one requirement may include determining whether the physician profile satisfies a financial requirement (320b). For example, the analysis engine 202 may determine whether a cost profile for a profiled physician satisfies the at least one requirement by determining whether the profiled physician satisfies a threshold level of cost effectiveness. As an example, the analysis engine 202 may determine a level of cost efficiency of the profiled physician generally or for a specific procedure. In some embodiments, the analysis engine 202 may analyze data associated with the physician although not explicitly in the profile, such as billing data, to make the determination. In other embodiments, the analysis engine 202 may analyze data associated with the physician but not in the profile at all. In one of these embodiments, for example, the analysis engine 202 accesses an eligibility lookup system (such as, for example, a system which may be provided by an insurance company) to determine whether, and to what extent, an insurance company covers one or more patient-physician interactions and whether the level of coverage satisfies the at least one requirement of the referral opportunity.

Determining that the physician profile satisfies the at least one requirement may include determining whether the physician profile satisfies an operational requirement (320c). For example, the analysis engine 202 may determine whether the profiled physician has availability in his or her schedule to undertake the referral opportunity, which may include an identification of a timeframe within which the referral appointment should take place. The analysis engine 202 may determine whether the profiled physician has staff available to undertake the referral opportunity. The analysis engine 202 may determine whether the geographic region or other location-based characteristic of the profiled physician satisfies the at least one requirement.

Determining that the physician profile satisfies the at least one requirement may include determining whether the physician profile satisfies a verification requirement (320d). In some embodiments, the first computing device 106a provides functionality both for identifying a profiled physician who satisfies the requirements of the potential referral and for connecting the profiled physician with the patient. In one of these examples, after the analysis engine 202 determines that the profiled physician satisfies the requirements of the potential referral, the first computing device 106a completes a verification process as part of the process of connecting the profiled professional with the patient. For example, the workflow engine 208 may maintain a state for each part of the verification process and generate a notification at the completion of each required stage. By way of example, in an embodiment in which the potential referral specified a requirement relating to insurance, the workflow engine 208 may maintain a state for a request, by the analysis engine 202, from an insurance company or a remote machine 106b associated with the insurance company, for confirmation of eligibility of a patient to see a profiled physician.

As an additional example of determining whether the physician profile satisfies a verification requirement, the workflow engine 208 may verify association with a network (including, e.g., hospital networks, accountable care networks, or other organizational structure of a hospital system). As another example of determining whether the physician profile satisfies a verification requirement, the workflow engine 208 may verify patient eligibility verification, including, for example, insurance verification, and other patient-oriented verification metrics. As an additional example of determining whether the physician profile satisfies a verification requirement, the workflow engine 208 may verify one or more credentials, including, for example, such factors as whether the profiled professional has an active license and no disciplinary actions.

In some embodiments, the first computing device 106a provides feedback to one or more other computing devices throughout the process of analyzing profiles and selecting profiled physician who qualify for one or more potential referrals. For example, the first computing device 106a may provide feedback to a second computing device 102 identifying characteristics of a potential referral that impacted the selection of a profiled physician or entity. As another example, the first computing device 106a may provide feedback to a profiled physician identifying attributes of the profile that impacted the qualification of the profiled physician for a potential referral. As another example, the workflow engine 208 may provide feedback to various computing devices identifying points in a verification process at which particular profiles were approved or filtered out (e.g., indicating to a referring physician that no insurance company would cover a particular type of referral or indicating to a profiled professional that he or she did or did not qualify for a referral opportunity based on insurance plans accepted, hours available, geography served, or other characteristic).

In some embodiments, the analysis engine 202 leverages both static and dynamic attributes in the profile when generating a potential referral. In other embodiments, the analysis engine 202 uses ranking to satisfy a plurality of requirements, which, as indicated above, may include requirements regarding availability, competency, financing, and operational constraints. In one of these embodiments, the analysis engine 202 is able to satisfy two or more constraints providing an improved experience. By way of example, and without limitation, a first physician may match all constraints but the analysis engine 202 may also identify a second physician that matches a subset of the constraints and that the analysis engine 202 determines to include in an enumeration of potential referrals. In another of these embodiments, a user can control the requirements evaluated by the analysis engine 202. For example, and without limitation, any user of the system, including profiled physicians, physicians requesting recommendations for referrals, patients or patient representatives of any type, or operators, may access a user interface to specify the one or more requirements. Such interfaces may also allow users to sort referral recommendations by the at least one requirement (e.g., specifying a requirement by which the list should be sorted). In still another of these embodiments, the analysis engine 202 uses dynamic information to do the ranking (e.g., dynamically updated as described above). In another of these embodiments, the system 200 provides functionality for requesting referral recommendations in real-time (e.g., referral recommendations based upon data retrieved and updated at substantially the same time as the request is received).

In some embodiments, the at least one requirement is a plurality of requirements, and the analysis engine 202 assesses each profile according to the plurality of requirements. In one of these embodiments, given a profile that has a plurality of attributes at least some of which are dynamically updated at a high frequency, the system 200 provides functionality for matching one or more of the plurality of constraints requested with one or more profiles that match at least a subset of the constraints. For example, a patient may indicate she wishes to work with a physician who is a female and is available for an annual visit in the next week and can meet at a location within 5 miles of the patient's home; the patient may further indicate that if such a professional is available, the patient would like to schedule a visit to see this physician. There may be other providers that partially satisfy the specified constraints. In some embodiments, the analysis engine 202 scores a match between the plurality of requirements and each profile and then ranks the identified profiles based on a rank ordering of the scores. The analysis engine 202 may create a potential referral for the highest-ranking profile. Continuing with the example above, the analysis engine 202 may determine that at least one physician is female and is available for an annual visit within the requested time period (seven days from the date of the request) but the at least one physician is not available to meet within a five-mile radius of the patient's home; in such an instance, the analysis engine 202 may rank those physicians that match a maximal set of constraints ahead of providers who match partial constraints.

In another example, the analysis engine 202 may determine that there are no physicians who satisfy all of the constraints but several physicians who each may satisfy a partial set of constraints; in this example, the analysis engine 202 provides high quality scoring of results and consequent ranking in order to identify non-matching physicians that still provide utility for the requesting user. Continuing with this example, the analysis engine 202 may determine that one set of physicians includes: a first physician who is female, has availability in two weeks for an annual visit, and is located within 15 miles of patient's home; a second physician who is male, has availability in one week for an annual visit, and is located within 5 miles of patient's home; and a third physician who is female, has availability in three weeks for an annual visit, and is located within 15 miles of patient's home. As each of the physicians represents a partial match to the requirements in the example, the analysis engine 202 may rank the physicians according to the number of matched criteria; for instance, the second profile may receive a higher ranking because it matches two of the requirements while the other two profiles match only one requirement each.

The weight assigned to each requirement may be automatically inferred based on the behavior of users who have used the system. For example, the system may show users alternate orderings of the different sets of providers described above and, based on the selections users have made in the past, may infer that a particular ordering may be preferred by users. The analysis engine 202 may use standard statistical techniques such as correlation as well as modern methods such as machine learning to generate such inferences.

In some embodiments, the analysis engine 202 ranks partially matching profiles by assigning varying weights to each of the plurality of requirements. For instance, in the above example, the analysis engine 202 may confer a higher weight on the requirement that the physician is female, and a lesser weight on distance requirements, so that a female physician available this week who is 7 miles from the patient's house is ranked higher than a male physician available this week who is 5 miles from the patient's house; such weights may be assigned based on patient-specified preferences, pre-defined rules, needs of a health system, or other basis for prioritization of requirements.

The weight assigned to each requirement may be defined specifically based on the needs of a particular health system. For example, a health system may define additional attributes that may be used for ranking the returned provider list. As a non-limiting example, given the relatively skilled resource that a doctor represents, health systems increasingly are trying to have nurse practitioners see many types of cases for which they are clinically appropriate. Attaining the credential of a nurse practitioner does not require as much education as attaining the credential of a medical doctor. Thus, nurse practitioners tend to be less expensive resources in the health system at large for providing health care. Consequently, a health system may impose a requirement that a case of the common cold be seen by a nurse practitioner, and require that an internal medicine doctor see a case of mild chest pain. The health system may encode such a business rule using the features provided by the system 200 so that when the analysis engine 202 generates an enumeration of profiles that match the requirements specified in requests for referrals, the analysis engine 202 is able to include such additional business rules when computing scores and ranking the order of the profiles. In some embodiments, the additional requirements are included in the entity profile of the institution corresponding to the health system; the additional requirements may also be included in the profile of each professional associated with the institution.

Certain requirements may be associated with an indication as to whether they are optional or can be relaxed (such requirements may be said to have the property that they cannot be relaxed). In some embodiments, and as a result of a requirement having such a property, the analysis engine 202 may omit all profiles that do not match the requirements. For example, chemotherapy treatment for a cancer patient is time-sensitive, and therefore if no physician can be found to match that constraint, the operator may be notified that no physician matches a required constraint. The operator may be moved into an alternate workflow as a result; for example, the operator may be asked to transfer the patient to a specific phone number to get additional assistance.

Other requirements may be assigned a degree of importance or of latitude in applying the requirement—that is, instead of being requirements, it may be optional to apply the constraint. In one embodiment, a requirement represents the preferences of a patient, such as the preference for a female doctor. In another embodiment, an optional requirement represents a preference of the health system, such as a preference for nurse practitioners over doctors when both sets of providers are clinically qualified to see the same condition. An optional requirement may reflect a preference of a physician. For example, a neurosurgeon may prefer not to see headaches and the health system may prefer that the neurosurgeon only see complex neurosurgery cases even though a neurosurgeon is clinically qualified to see a patient with a headache.

When attempting to identify profiles that satisfy the constraints specified in the request, the analysis engine 202 may use all available profile information. Such information would include information that is updated in real-time. For example, the available appointment slots for a physician will change as soon as an appointment is booked and the analysis engine 202 may include functionality to use the updated availability data in subsequent searches in order to provide an accurate enumeration of profiles that fulfill (partially or completely) constraints specified in the request.

Where the requirements pertain to profile attributes that are subject to rapid change through an updating process as described above in reference to FIGS. 2A-2D, the analysis engine 202 may update the ranking to reflect modifications to the attributes. Returning to the above example, the female physician within 5 miles of the patient's home and available for a visit next week may have a change of schedule, which is automatically updated to her profile, indicating that she is no longer available for an appointment next week; the ranking may be modified to give a higher ranking to a second provider who is female, available next week, and located 7 miles away.

Other examples of dynamically updated information include clinical skills associated with the population of healthcare providers. While the clinical skills associated with a single provider may not change frequently, the clinical skills associated with a population of providers may change multiple times per day as new clinicians are added, existing clinicians leave, and some clinicians change their skill sets. Such information may be updated as soon as it becomes available so that subsequent searches accurately identify an enumeration of profiled physicians that satisfy (partially or completely) the requirements of the subsequent searches; the analysis engine 202 may use the updated information to recalculate the degree to which a profile matches the requirements and to modify the corresponding ranking. Dynamic constraints are important inputs into the scoring computation that is used when providers partially match the constraints specified in the request. By incorporating dynamic information into such scoring computations, the analysis engine 202 improves the utility of the ordered results, avoiding returning suboptimal rank orders relative to the original request.

In some embodiments, the use of dynamically updated data collected in a manner that balances performance constraints, the speed at which different categories of data change, and the relative importance of different categories of data enables the analysis engine 202 to generate recommendations for referrals based on current, accurate information. In other embodiments, the use of near-instant electronic communication between the analysis engine 202, profile generator 204, and administrative or clinical machines at distributed locations allows the system 200 to greatly exceed the scheduling capabilities of traditional scheduling platforms, particularly in fields such as medicine where accurate management of complex factual situations is particularly crucial.

Referring again to FIG. 3A, the method 300 includes providing, by the analysis engine, to the call center, the potential referral during the call (310). In some embodiments, the analysis engine 202 generates the identification of profiled physicians that satisfy the at least one requirement in near real time, that is, at substantially the same time as the request for the identification is received. In one of these embodiments, this functionality provides increased usability in implementations in which the operator will interact with the system to review the results contained in the responses, then generate, reformulate, or modify the operator's query if none of the results are satisfactory, and then resubmit the operator's query; for instance, the operator may review one or more potential referrals to physicians as produced by the analysis engine 202, describe the one or more potential referrals to the patient, and then modify the at least one requirement to generate a new list of potential referrals, based on feedback from the patient. In another of these embodiments, by providing functionality with which the analysis engine 202 may evaluate multiple combinations of criteria substantially simultaneously, the system provides improved usability.

In some embodiments, the presentation engine 212 presents at least one potential referral to the operator using a user interface 214. For instance, the user interface 214 may display at least one potential referral to the operator using a display device 124a-n as described above in reference to FIGS. 1A-1C. The user interface 214 may provide the at least one potential referral to the operator by audio means, using a headset (e.g., having computer-generated speech played to the operator over the headsets). In some embodiments, the user interface 214 presents a plurality of potential referrals in a default order. For instance, the user interface 214 may present a plurality of potential referrals in order of a ranking of suitability to fit the one or more at least one requirement, as described above in reference to FIG. 3A. The operator may also be able to enter one or more criteria to sort the result set. In addition to returning results from the analysis engine 202 in the order determined by a scoring computation (e.g., rank-ordering algorithm), in some embodiments, the system 200 allows the operator to retrieve results ordered by one or more criteria (e.g., sorted by last name, sorted by distance, sorted by availability, etc.). The operator may enter instructions creating a nested sort, for example by having the results ordered first by the nearest week in which the physicians are available, and second by the distance from the patient's house. In some embodiments, the analysis engine 202 indicates result rankings so determined even when the results are ordered according to a user-entered sorting criterion; for instance, the analysis engine 202 may display a cardinal number next to each result corresponding to the result's determined ranking.

In some embodiments, the operator reviews the identification of the at least one of the professional and the entity, and decides that none of the results are satisfactory. The operator may determine upon reviewing the results that none of the potential referrals presented is likely to meet the patient's needs. The operator may describe the at least one potential referral to the patient, who may inform the operator that the at least one potential referral is unsatisfactory. The operator may then enter a new instruction modifying the at least one requirement. In some embodiments, the analysis engine 202 determines that at least one second profile satisfies the at least one requirement as modified; the analysis engine 202 may perform this determination as disclosed above in reference to FIG. 3A. The analysis engine 202 may be able to perform the re-determination in substantially real time, ensuring that the determination is performed using current information. In some embodiments, in addition to computing the set of valid providers based upon the updated criteria, the analysis engine 202 also displays partial matches as described above in reference to FIG. 3A.

In some embodiments, the analysis engine 202 computes and returns the valid attribute values for each requirement that could be used to further subset the results, without ending the search with a null result set; as a result, if the operator has added such an attribute value to their query criteria, the resulting set of matching physicians may return results that do not match that value, and indicate that no results matched the value. By way of example, the operator could add the attribute value to a new search (e.g., a search within the search results) in order to further narrow the results. In some embodiments, allowing the operator to interactively modify the requirements allows the operator to choose the criteria that matter to the patient interactively so that the operator can find a physician who best matches the patient's needs. Each selection of a new requirement by the operator may cause the presentation engine 212 to organize new results in subsets, allowing the user to see the effect of the new requirement. The user may also be able to remove requirements; the analysis engine 202 may then find one or more profiles matching the at least one requirement absent the removed requirements, as disclosed above in reference to FIG. 3A.

In another embodiment, the analysis engine 202 is able to filter out criteria that would lead to zero results, improving user experience since the set of all possible combinations of filter values is significantly larger (e.g., by many orders of magnitude) than the set of valid (e.g., non-zero) combinations of filter values, where a valid combination of filter values is one that can be satisfied by at least one profiled professional. In some embodiments, the system 200 leverages existing user interface technology such as, without limitation, guided navigation, guided search, or faceted search interfaces.

The user interface 214 may continuously update the data provided to the operator, such as the patient data or data produced by speech-to-text algorithms as described above in reference to FIG. 3A, as new data is received; for instance, the user interface 214 may implement a loop that periodically sweeps for new or modified data and provides the new or modified data to the operator. The operator may be able to modify the data as well; for instance, the user interface 214 may receive one or more instructions from the operator modifying data that has been provided to the operator. The presentation engine 212 may modify the data as instructed, so that future displays of the data to the operator contain the modifications.

As a non-limiting example, a patient may call the call center, provide identifying information, for instance in response to an operator prompt such as "can you state your name," and describe a medical need to the operator; the speech-to-text converter may capture the patient's identifying information and description of medical needs, and display both to the operator via the user interface 214, with the operator verifying each with the patient. Continuing the example, the analysis engine 202 may obtain electronic medical records matching the patient identity from a remote machine 106b, use the medical history in the electronic medical records, combined with the call data received from the second computing device 102, to generate a list of probable patient needs, which the user interface 214 may display to the operator; the operator may ask the patient if the patient wishes to fulfill each of the listed probable needs until obtaining a confirmed set of medical procedures or other tasks the patient would like to have performed. Further continuing the example, the operator may ask the patient for preferences, such as geographical preferences or preferences regarding the sex of the physician who will perform the needed service; further patient preferences may be retrieved from the electronic medical records or the profile generator 204. Continuing the example, the operator may confirm the at least one requirement, and the analysis engine 202 may generate a list of potential referrals, describing the physicians who may be able to perform the services, and who match the at least one requirement; upon hearing the potential referrals, the patient may indicate a selection of a referral which the operator will then confirm, for instance by verifying the location, time, and physician with the patient, and scheduling an appointment.

In some embodiments, the analysis engine 202 determines that the physician whose profile was selected for the potential referral is not available, generates a second potential referral to a second physician for the patient, the physician having a profile that satisfies the determined at least one requirement, and provides, to the call center, the second potential referral during the call. For example, a patient may call the call center asking for an appointment with a particular doctor, Dr. Smith, thus making the at least one requirement a requirement for Dr. Smith specifically; the operator may attempt to enter the potential appointment, and the analysis engine 202 may return a result indicating that Dr. Smith is not available within six months of the call. Continuing the example, the operator may determine that six months is too far in the future, either because the patient states that such a long wait is unacceptable, or because the category of appointment needed is recorded in the system 200 as an urgent appointment, such as a chemotherapy session. Further continuing the example, the operator may direct the analysis engine 202 to search for similar doctors as substitutes, and the analysis engine 202 may determine that Dr. Jones is similar to Dr. Smith according to criteria described above in reference to FIGS. 3A-3D; the operator may confirm that the patient is willing to see Dr. Jones, prior to scheduling an appointment with Dr. Jones.

In some embodiments, the workflow engine 208 schedules an appointment with the physician corresponding to the potential referral for the patient. In some embodiments, the workflow engine 208 transmits a message to the physician requesting that the physician provide availability data, receives a message from the physician describing availability data, and schedules the appointment using that availability data; the request may be sent on a regular basis, so that the availability data is updated prior to the call. The request may include a range of dates and times within which availability data is sought; for instance, if the appointment must be completed within two months of the referral, the request may ask the physician to indicate availability within that two-month window. Availability data may include dates and times during which the professional is available to engage in the appointment to be scheduled. The workflow engine 208 may use any means for communication via a network to send and receive the messages. For example, the workflow engine 208 may send the professional an electronic mail (email) message requesting the dates and times the physician has available. The physician may send the workflow engine 208 an email in response listing dates and times. In some embodiments, the presentation engine 212 provides to the physician a user interface by means of which the physician can enter availability data. For example, and without limitation, the presentation engine 212 may provide an interactive calendar into which the physician may enter dates and times of availability. In some embodiments, the workflow engine 208 receives availability data from a remote device 106b. As an example, the workflow engine 208 may receive availability data from a remote device 106b that maintains schedule information at the physician's place of employment.

In some embodiments, the availability data includes information describing the degree of urgency of already-scheduled appointments. In some embodiments, the availability data contains a description of the activity to take place in each scheduled appointment. In some embodiments, the availability data contains a standardized description of the activity to take place, such as an ICD code corresponding to the activity. In some embodiments, the availability data contains a description of the condition of a patient to be treated during an already-scheduled appointment. The availability data may describe the age of the patient. The availability data may describe the medical history of the patient. The availability data may describe the risk factors attendant to the treatment of the patient. The availability data may describe a current medical condition of the patient. In some embodiments, the availability data describes a condition of the patient using a standardized system, such as the ICD. In some embodiments, the availability data contains a ranking of the urgency of the already-scheduled appointment, with a higher ranking for an appointment that is more immediately necessary, and a lower ranking for an appointment that can be postponed more safely.

In some embodiments, the workflow engine 208 compares the urgency of an already scheduled appointment with the urgency of the appointment to be scheduled. The workflow engine 208 may generate a ranking for the urgency of the appointment to be scheduled, and compare that ranking to the ranking of the urgency of the already scheduled appointment. The workflow engine 208 may compare the state of health of the subject of the referral to the state of health of the patient in the already-scheduled appointment. For example, an appointment for an elderly person may be treated as more urgent than an appointment for a younger person, other factors being equal. In some embodiments, the condition to be treated in the appointment to be scheduled is described in a standardized form such as the ICD. In some embodiments, the workflow engine 208 compares the urgency of the treatment to be administered in the appointment to be scheduled with the urgency of the treatment to be administered in the already-scheduled appointment. In some embodiments, the treatment to be administered in the appointment to be scheduled is described using a standardized system, such as the ICD. In some embodiments, the workflow engine 208 follows a ranking protocol for the treatment of patients; for example, the workflow engine may follow a hospital's "triage" protocol for deciding which patient to treat first. In some embodiments, the workflow engine 208 calculates the relative ranking of the two appointments by following a set of protocols; for example, weighting the urgency of each appointment according to the urgency of each individual factor described above.

In some embodiments, the workflow engine 208 consults a table or similar data structure listing the ranking of various appointments according to several factors.

In some embodiments, the workflow engine 208 reschedules an already-scheduled appointment if a comparison to the appointment to be scheduled reveals the latter to be more urgent. For instance, if the patient in the already-scheduled appointment is scheduled for an elective surgery whose outcome is unlikely to be affected by a delay, and the subject of the referral is being scheduled for an appendectomy, the elective surgery may be rescheduled to make room for the appendectomy. In some embodiments, the workflow engine 208 avoids rescheduling already-scheduled appointments if alternative times for the appointment to be scheduled are available. In some embodiments, the workflow engine 208 only reschedules an already-scheduled appointment if the rescheduling is medically necessary. In some embodiments, a user of the system may override the decision of the workflow engine 208 to reschedule; for instance, the professional to whom the referral is made may reject the rescheduling decision as contrary to his or her medical judgment, and enter an instruction overriding the rescheduling.

In some embodiments, the workflow engine 208 selects an appointment time from the availability data. The workflow engine 208 may select the appointment time by comparing the availability data to data indicating the availability of the patient. In some embodiments, the workflow engine 208 selects the earliest available date and time for the appointment time. In some embodiments, the first computing device 106a receives at least one preferred date and time from the patient, and the workflow engine 208 selects an appointment time corresponding to the at least one preferred date and time.

In some embodiments, the workflow engine 208 determines an amount of time required by the physician for the appointment. The workflow engine may determine the amount of time required by accessing the physician's profile; as an example, the workflow engine 208 may determine from the profile that the physician typically performs the type of appointment in question within 45 minutes. The workflow engine 208 may receive from the physician data indicating the amount of time required. The amount of time required may be included in the availability data. The workflow engine 208 may determine the amount of time required by calculating the typical amount of time physicians take to perform the type of appointment in question; for instance, the workflow engine 208 may access data describing the length of appointments of the type under consideration, and compute the median time required to complete the appointments recorded in that data. The workflow engine 208 may select an appointment time only if the availability data indicates that the availability data permits an appointment of at least the time required by the physician for the appointment, at that time.

In some embodiments, the workflow engine 208 determines that at least one resource required for the appointment is available. A resource may be a room in which the appointment would take place. For example, if the appointment is a surgical procedure, the workflow engine 208 may only select an appointment time during which an operating room is available. A resource may be a piece of equipment necessary for the appointment. For instance, the workflow engine 208 may only schedule an endoscopic procedure for a time when the required type of endoscopic device is available. A resource may be another professional necessary for the appointment; the workflow engine 208 may schedule a surgical procedure for a given time only if an anesthesiologist is available at that time. In some embodiments, the appointment requires a particular combination of resources, and the workflow engine 208 selects an appointment time in which the entire combination is available. A non-limiting example is a neurosurgical procedure that requires an operating room with an installed robotic surgical system, a complementary set of imaging technologies, a team of radiologists, technicians with specialized training, several nurses, and an anesthesiologist all to work together throughout the procedure.

The workflow engine 208 may obtain availability data for resources in any manner disclosed above. The workflow engine 208 may receive availability data from the physician, for instance via the user interface 214 described above. The workflow engine 208 may receive the availability data from a remote machine 106b, such as a machine that stores scheduling information for the institution at which the physician works. If the resource is not available, the workflow engine 208 may request the identification of another physician from the analysis engine 202. In some embodiments, the analysis engine 202 queries the workflow engine 208 regarding availability of one or more resources as part of determining that the generated profile of a physician satisfies at least one requirement.

In some embodiments, the workflow engine 208 automatically reserves at least one resource for the potential referral. In some embodiments, reserving the at least one resource involves reserving at least one room in which the appointment will occur. In some embodiments reserving the at least one resource involves reserving at least one item of equipment to be used during the appointment. In some embodiments reserving the at least one resource involves scheduling an additional physician or other professional to take part in the appointment. The workflow engine 208 may reserve a set of resources required for the appointment. In some embodiments, the workflow engine 208 determines the availability of each resource to be reserved as described above in reference to FIG. 3A. The workflow engine 208 in some embodiments transmits a request to reserve the at least one resource to a remote device 106b; for instance, the workflow engine 208 may transmit a request to reserve the at least one resource to a remote device 106b that maintains schedule information for the institution at which the physician works. In some embodiments, the workflow engine 208 provides a request to reserve the at least one resource to a person; for instance, the workflow engine 208 may send an email to a person responsible for scheduling the at least one resource.

In some embodiments, the workflow engine 208 may rank a plurality of resources, for a particular type of resource, and select the highest-ranking available resource. The workflow engine 208 may use any approach disclosed above for ranking profiles of professionals or entities in reference to FIG. 3A to rank the plurality of resources. The workflow engine 208 may rank the plurality of resources according to the preference of the physician. In some embodiments, the workflow engine 208 receives the preference of the physician from the physician. In some embodiments, the profile generator 204 maintains, in the physician's profile, data indicating the physician's preferences with regard to a type of resource. In some embodiments, the analysis engine 202 determines the likely preferences of the physician by analyzing past selections the physician made when deciding which resource of that resource type to use. In some embodiments, the profile generator 204 generates profiles for resources, as disclosed above in reference to FIG. 3A. In some embodiments, the profile generator 204 maintains data in the profiles of resources indicating each resource's effectiveness. The effectiveness of a resource may be calculated using data concerning patient outcomes. The effectiveness of a resource may be calculated using feedback of physicians. The effectiveness of a resource may be calculated using patient feedback. The effectiveness of a resource may be calculated by determining the number of times the resource has been selected for the kind of appointment to be scheduled in the past. The effectiveness of a resource may be calculated by reference to information concerning its manufacture, where the resource is a piece of equipment; for instance, a piece of equipment that is newer may be ranked higher than an otherwise identical piece of equipment that is older. Where the resource is a physician or other professional, the resource may be ranked according to degree of expertise in a category of expertise relevant to the appointment to be scheduled.

In some embodiments, the workflow engine 208 ranks resources according to patient preferences. The workflow engine 208 may rank resources by logistical convenience to the patient; for instance, the workflow engine 208 may give a possible room in which the appointment will take place a higher ranking if it is closer to the home of the patient. Likewise, where the choice of resources is pertinent to the right of the patient to make informed choices concerning his or her treatment, the choice of one particular resource over another by the patient may cause the workflow engine 208 to give the preferred resource a higher ranking. In some embodiments, the workflow engine 208 receives information concerning the preferences of the patient from the operator, via the second computing device 102. In some embodiments, the workflow engine 208 receives information concerning the preferences of the subject of the referral from the patient, via a computing device (not shown) used by the patient.

In some embodiments, the workflow engine 208 ranks a plurality of possible combinations of resources with the physician. The workflow engine 208 may compare the patient outcomes of different combinations; by way of an example, if the professional is a surgeon, and the physician's patients have a higher rate of complication-free recovery when the physician works with a particular team of nurses, the combination of that physician with that team will be given a higher rank.

In one embodiment, therefore, the methods and systems described herein provide functionality for data-driven management of referrals by call center operators, in a manner that records the occurrence of such referrals, and uses that occurrence as additional data to aid in future referral management, while automatically and in real-time modifying graphical user interfaces rendered for display at a call center during the call to reflect updated information regarding the operator interaction with the user and the identified referrals.

Although some of the examples provided herein describe the analysis in connection with the medical profession, the legal profession, and other professional service industries, one of ordinary skill in the art will understand that the methods and systems described herein are equally applicable in other industries. Similarly, although the description above categorizes professionals as industry professionals (such as providers of goods or services), professionals such as physicians, and employers of professionals, it should be understood that any one individual may be categorized as any one or more of these types of professionals; for example, an industry professional need not be a vendor but could be a physician seeking to provide an opportunity to another physician and an employer in a particular instance may be better categorized as an industry professional. As discussed in an example given above, a hiring manager in a business (e.g., an employer) may evaluate the behavior of a career development officer at an academic institution (e.g., an industry professional) to determine whether the career development officer is influential with graduating students (e.g., professionals) whom the business wishes to hire.

It should be understood that the systems described above may provide multiple ones of any or each of those components and these components may be provided on either a standalone machine or, in some embodiments, on multiple machines in a distributed system. The phrases 'in one embodiment,' 'in another embodiment,' and the like, generally mean the particular feature, structure, step, or characteristic following the phrase is included in at least one embodiment of the present disclosure and may be included in more than one embodiment of the present disclosure. Such phrases may, but do not necessarily, refer to the same embodiment.

The systems and methods described above may be implemented as a method, apparatus, or article of manufacture using programming and/or engineering techniques to produce software, firmware, hardware, or any combination thereof. The techniques described above may be implemented in one or more computer programs executing on a programmable computer including a processor, a storage medium readable by the processor (including, for example, volatile and non-volatile memory and/or storage elements), at least one input device, and at least one output device. Program code may be applied to input entered using the input device to perform the functions described and to generate output. The output may be provided to one or more output devices.

Each computer program within the scope of the claims below may be implemented in any programming language, such as assembly language, machine language, a high-level procedural programming language, or an object-oriented programming language. The programming language may, for example, be LISP, PROLOG, PERL, C, C++, C#, JAVA, or any compiled or interpreted programming language.

Each such computer program may be implemented in a computer program product tangibly embodied in a machine-readable storage device for execution by a computer processor. Method steps of the invention may be performed by a computer processor executing a program (e.g., computer program instructions) tangibly embodied on a non-transitory computer-readable medium to perform functions of the invention by operating on input and generating output. Suitable processors include, by way of example, both general and special purpose microprocessors. Generally, the processor receives instructions and data from a read-only memory and/or a random access memory. Storage devices suitable for tangibly embodying computer program instructions include, for example, all forms of computer-readable devices; firmware; programmable logic; hardware (e.g., integrated circuit chip; electronic devices; a computer-readable non-volatile storage unit; and non-volatile memory, such as semiconductor memory devices, including EPROM, EEPROM and flash memory devices); magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive programs and data from a storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium. A computer may also receive programs and data from a second computer providing access to the programs via a network transmission line, wireless transmission media, signals propagating through space, radio waves, infrared signals, etc.

Having described certain embodiments of methods and systems for analyzing speech to generate a potential referral, it will now become apparent to one of skill in the art that other embodiments incorporating the concepts of the disclosure may be used. Therefore, the disclosure should not be limited to certain embodiments but rather should be limited only by the spirit and scope of the following claims.

What is claimed is:

1. A method for analyzing speech generated during a call to generate a potential referral and automatically modifying, during the call, a user interface displaying, to a call center operator generating a referral to a physician for a patient, data associated with the analyzed speech, the method comprising:
   receiving, during a call by a patient to a call center operator, by an analysis engine executing on a first computing device, from a second computing device executing a speech-to-text converter, data generated during a call by a patient to a call center operator by converting audio data to text data, the call center operator generating a referral to a physician for the patient;
   analyzing, by the analysis engine, the received data generated during the call, wherein analyzing further comprises:
      analyzing at least one acoustic feature of the patient speech during the call, the at least one acoustic feature identified in the received data, and
      identifying at least one keyword within the received data;
   identifying, by the analysis engine, patient data stored in an electronic medical record associated with the patient, responsive to the analysis of the identified at least one keyword;
   determining, by the analysis engine, at least one requirement of the patient based upon the identified patient data and the analysis of the at least one acoustic feature and of the identified at least one keyword;
   generating, during the call by the patient to the call center operator, by the analysis engine, a potential referral to a physician for the patient, the physician having a profile that satisfies the determined at least one requirement, based on the analysis of the at least one acoustic feature and of the identified at least one keyword; and
   modifying, by a presentation engine executing on the second computing device, a user interface displayed to the call center operator, during the call by the patient to the call center operator, the modification to the user interface including addition to the user interface of an identification of the potential referral; and
   modifying, by the presentation engine, the user interface displayed to the call center operator, during the call by the patient to the call center operator, the modification to the display including addition to the user interface of an identification of feedback to the call center operator regarding an emotional state of the patient, based on the analysis of the acoustic feature and of the identified at least one keyword.

2. The method of claim 1, wherein analyzing further comprises identifying, by the analysis engine, sentiment data including an identification of a sentiment expressed by the patient.

3. The method of claim 1, wherein analyzing further comprises identifying, by the analysis engine, an emotional state of the patient.

4. The method of claim 3, wherein determining the at least one requirement of the patient includes determining a level of urgency of a patient need based upon the identified emotional state of the patient.

5. The method of claim 3, wherein modifying further comprises modifying the user interface, during the call, to include feedback to the agent regarding the patient emotion.

6. The method of claim 1, wherein analyzing further comprises identifying, by the analysis engine, at least one personality trait of the patient.

7. The method of claim 6, wherein determining the at least one requirement of the patient further comprises determining a characteristic of a physician with a complementary personality trait to the identified at least one personality trait of the patient.

8. The method of claim 1, wherein identifying further comprises identifying, by the analysis engine, within a record accessible to the call center, the patient data.

9. The method of claim 1, wherein identifying further comprises identifying, by the analysis engine, an electronic medical record associated with the patient.

10. The method of claim 1, wherein determining further comprises matching, by the analysis engine, a key word identified within the received data to a term within a taxonomy system accessible to the first computing device.

11. The method of claim 1 further comprising determining, by the analysis engine, before generating the potential referral, that the profile satisfies a clinical effectiveness requirement.

12. The method of claim 1 further comprising:
determining that the physician is not available;
generating, by the analysis engine, a second potential referral to a second physician for the patient, the physician having a profile that satisfies the determined requirement; and
providing, by the presentation engine, to the call center, the second potential referral during the call.

13. A system for analyzing speech generated during a call to generate a potential referral and automatically modifying, during the call, a user interface displaying, to a call center operator generating a referral to a physician for a patient, data associated with the analyzed speech, the system comprising:
an analysis engine executing on a first computing device and:
 (i) receiving, during a call by a patient to a call center operator, from a second computing device executing a speech-to-text converter, data generated during a call by a patient to a call center operator by converting audio data to text data, the call center operator generating a referral to a physician for the patient,
 (ii) analyzing, the received data generated during the call, wherein analyzing further comprises analyzing at least one acoustic feature of the patient speech during the call, the at least one acoustic feature identified in the received data and identifying at least one keyword within the received data,
 (iii) identifying patient data stored in an electronic medical record associated with the patient, responsive to the analysis of the identified at least one keyword,
 (iv) determining at least one requirement of the patient based upon the identified patient data and the analysis analysis of the at least one acoustic feature and of the identified at least one keyword,
 (v) generating, during the call by the patient to the call center operator, a potential referral to a physician for the patient, the physician having a profile that satisfies the determined at least one requirement, based on the analysis of the at least one acoustic feature and of the identified at least one keyword; and
a presentation engine executing on the second computing device and (i) modifying a user interface displayed to the call center operator, during the call by the patient to the call center operator, the modification to the user interface including addition to the user interface of an identification of the potential referral and (ii) modifying the user interface displayed to the call center operator, during the call by the patient to the call center operator, the modification to the display including addition to the user interface of an identification of feedback to the call center operator regarding an emotional state of the patient, based on the analysis of the acoustic feature and of the identified at least one keyword.

* * * * *

UNITED STATES PATENT AND TRADEMARK OFFICE
CERTIFICATE OF CORRECTION

PATENT NO. : 10,691,407 B2  
APPLICATION NO. : 15/840586  
DATED : June 23, 2020  
INVENTOR(S) : Yoo et al.

Page 1 of 1

It is certified that error appears in the above-identified patent and that said Letters Patent is hereby corrected as shown below:

In the Specification

In Column 5, Line 4, delete "medium 116" and insert -- device 116 --, therefor.

In Column 5, Line 62, delete "SCL/LAMP" and insert -- SCI/LAMP --, therefor.

In Column 18, Line 64, delete "102b" and insert -- 102a --, therefor.

In Column 24, Line 37, delete "Mill" and insert -- MRI --, therefor.

In the Claims

In Column 46, Lines 6-7, Claim 13 delete "the analysis analysis of" and insert -- the analysis of --, therefor.

Signed and Sealed this  
First Day of September, 2020

Andrei Iancu  
*Director of the United States Patent and Trademark Office*